US008469970B2

(12) United States Patent
Diamant et al.

(10) Patent No.: US 8,469,970 B2
(45) Date of Patent: Jun. 25, 2013

(54) APPARATUS FOR ENTRAPPING AND EXTRACTING OBJECTS FROM BODY CAVITIES

(75) Inventors: Valery Diamant, Katzrin (IL); Chaim Lotan, Jerusalem (IL); Haim Danenberg, Jerusalem (IL)

(73) Assignee: Great Aspirations Ltd., Katsrin (IL)

( * ) Notice: Subject to any disclaimer, the term of this patent is extended or adjusted under 35 U.S.C. 154(b) by 94 days.

(21) Appl. No.: 13/179,750

(22) Filed: Jul. 11, 2011

(65) Prior Publication Data
US 2013/0018387 A1    Jan. 17, 2013

(51) Int. Cl.
A61B 17/22 (2006.01)

(52) U.S. Cl.
USPC .......................................................... 606/127

(58) Field of Classification Search
USPC ................. 606/110, 111, 112, 113, 114, 115, 606/127, 128, 200
See application file for complete search history.

(56) References Cited

U.S. PATENT DOCUMENTS

| 1,722,474 | A | 7/1929 | Langhein |
| 3,828,790 | A | 8/1974 | Curtiss et al. |
| 4,326,530 | A | 4/1982 | Fleury, Jr. |
| 4,873,978 | A | 10/1989 | Ginsburg |
| 5,098,440 | A | 3/1992 | Hillstead |
| 5,171,233 | A | 12/1992 | Amplatz et al. |
| 5,171,314 | A | 12/1992 | Dulebohn |
| 5,300,086 | A | 4/1994 | Gory et al. |
| 5,417,684 | A | 5/1995 | Jackson et al. |
| 5,549,626 | A | 8/1996 | Miller et al. |
| 5,658,296 | A | 8/1997 | Bates et al. |
| 5,800,457 | A * | 9/1998 | Gelbfish ........................ 606/200 |
| 5,944,728 | A | 8/1999 | Bates |
| 5,993,474 | A * | 11/1999 | Ouchi ............................ 606/206 |
| 6,066,149 | A * | 5/2000 | Samson et al. ................. 606/159 |
| 6,077,274 | A * | 6/2000 | Ouchi et al. ................... 606/113 |
| 6,099,534 | A | 8/2000 | Bates et al. |
| 6,168,603 | B1 | 1/2001 | Leslie et al. |
| 6,280,451 | B1 * | 8/2001 | Bates et al. ................... 606/127 |
| 6,331,183 | B1 | 12/2001 | Suon |
| 6,458,145 | B1 | 10/2002 | Ravenscroft et al. |
| 6,491,698 | B1 | 12/2002 | Bates et al. |

(Continued)

FOREIGN PATENT DOCUMENTS

DE        19818468         10/1998
WO        WO 99/16363      4/1999

(Continued)

*Primary Examiner* — Ryan Severson
*Assistant Examiner* — Jonathan W Miles
(74) *Attorney, Agent, or Firm* — Frommer Lawrence & Haug LLP; William S. Frommer

(57) ABSTRACT

A retrieval apparatus for entrapping and retaining an object located in a body for its extraction therefrom is described. The retrieval apparatus includes a snare and a snare control assembly. The snare has a proximal section and a distal section, and comprises a plurality of filaments extending from a proximal end of the proximal section towards the distal section, and then returning to the proximal end to form a plurality of loops. In the deployed state, the loops are interlaced to each other within the proximal section and are free and not interleaved within the distal section. Segments of the filaments of the distal section are bent with respect to segments of the filaments of the proximal section such that the retrieval snare in the contracted state forms a hollow cavity extending from the distal section towards the proximal section.

45 Claims, 17 Drawing Sheets

U.S. PATENT DOCUMENTS

| | | |
|---|---|---|
| 6,506,209 B2 | 1/2003 | Ouchi |
| 6,527,781 B2 * | 3/2003 | Bates et al. .................. 606/114 |
| 7,169,154 B1 * | 1/2007 | Que et al. ..................... 606/127 |
| 7,837,702 B2 | 11/2010 | Bates |
| 8,167,901 B2 * | 5/2012 | Hendriksen et al. .......... 606/200 |
| 8,298,244 B2 * | 10/2012 | Garcia et al. ................. 606/127 |
| 2003/0009177 A1 * | 1/2003 | Middleman et al. .......... 606/127 |
| 2005/0165441 A1 | 7/2005 | McGuckin, Jr. et al. |
| 2006/0058838 A1 | 3/2006 | Bose et al. |
| 2007/0135820 A1 * | 6/2007 | Que et al. ..................... 606/127 |
| 2008/0009116 A1 | 1/2008 | Lee |
| 2008/0086149 A1 | 4/2008 | Diamant et al. |
| 2009/0163846 A1 | 6/2009 | Aklog et al. |
| 2009/0270808 A1 | 10/2009 | Mas et al. |
| 2010/0286709 A1 * | 11/2010 | Diamant et al. .............. 606/128 |

FOREIGN PATENT DOCUMENTS

| | | |
|---|---|---|
| WO | WO 2006/124405 | 11/2006 |
| WO | WO 2008/041094 | 4/2008 |
| WO | WO 2009/074981 | 6/2009 |

* cited by examiner

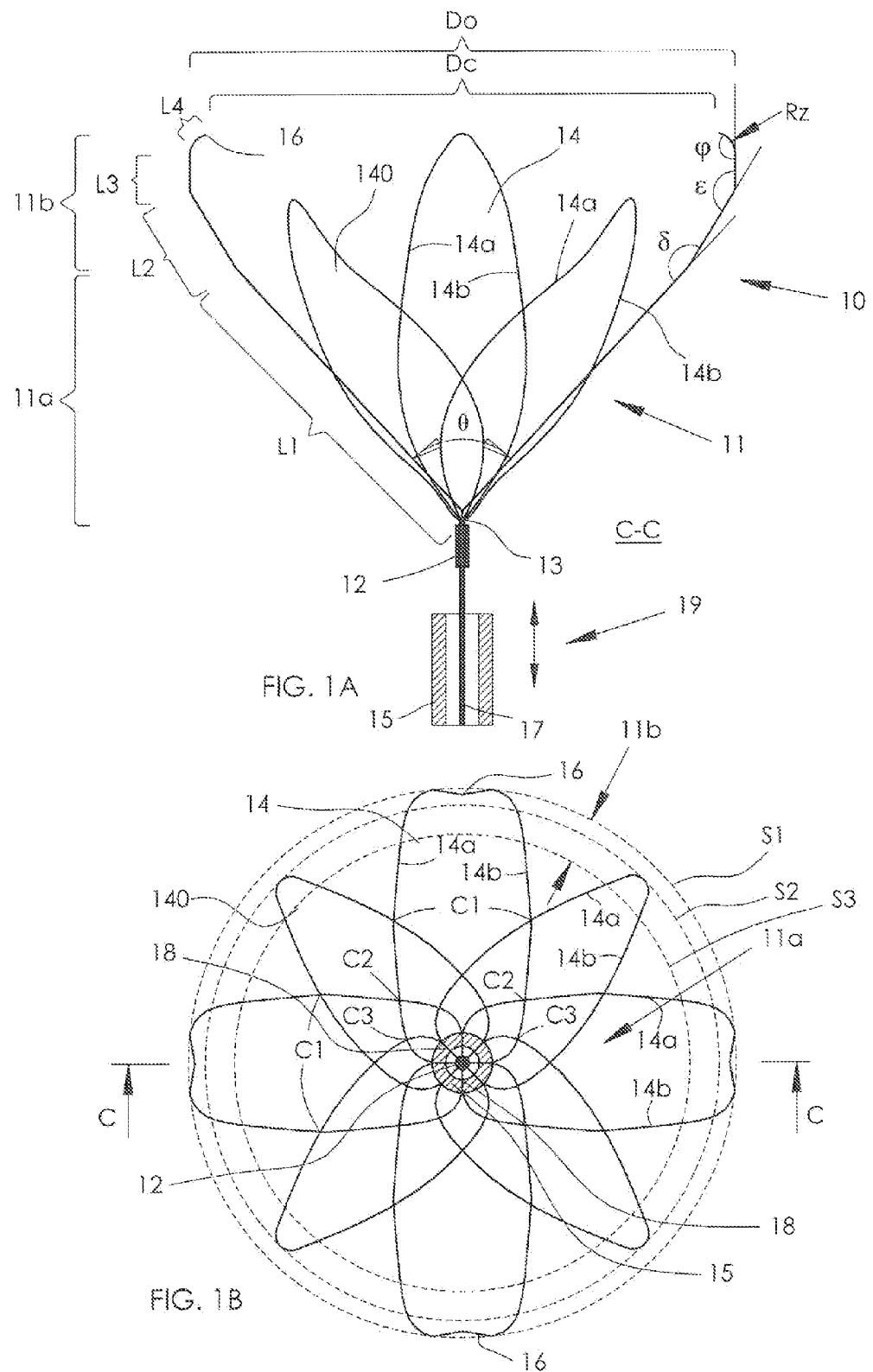

APPARATUS FOR ENTRAPPING AND EXTRACTING OBJECTS FROM BODY CAVITIES

FIELD OF THE INVENTION

The present invention relates to an extraction device capable of capturing and extracting objects from hollow bodies, and in particular, to a medical instrument for entrapping and removing an object from a body.

BACKGROUND OF THE INVENTION

Various instruments are known in the art for removing various objects from the body. For example, such instruments are used for removal of stones such as kidney stones, gallstones, and the like from various sites along the urinary tract of a patient's body. Retrieval devices are also widely used for removing foreign articles from the vascular system of a patient. In such a case, examples of the foreign articles include vena cava filters and parts of medical devices, such as catheters, guidewires, cardiac leads, etc., which may break and become detached during medical procedures.

Some types of these instruments employ a retrieval collapsible wire basket arranged within a flexible catheter formed as a tubular sheath adapted to penetrate body passages to reach the location from where the object is to be evacuated (see, for example U.S. Pat. Nos. 5,658,296; 6,168,603; and 6,491,698 to Bates et. al.). The basket and the sheath can move relative to each other to open and close the basket. The basket consists of flexible wires and is made of a material capable to provide the basket with elasticity. The wires are bound together in the vicinity of a basket proximal end as well as at a basket distal end. Depending on the manipulation, the basket may either retract inside the sheath, to allow penetration of the catheter via a passage, or protract from the catheter. In the protracted position, the basket is open, due to the elasticity of the wire material, and forms a cage to thus allow entrance of the object into the basket through the open spaces left between its adjacent wires. Further retraction of the basket into the sheath results in the cage collapsing and entrapping the object in the basket. Removal of the catheter will enable the whole device to be removed from the body organ together with the object immobilized within the basket. During an operation, the operator moves the catheter behind the object to be extracted, and then protracts the basket from the catheter. Once the basket is protracted, it opens (due to its resiliency), and is ready for receiving the object to be entrapped therein. The operator pulls the catheter together with the basket until it entraps the object, and then extracts the entrapped object from the body.

Another type of retrieval device includes miniaturized grasping forceps configured for grasping the foreign body anywhere along its length. For example, U.S. Pat. Nos. 5,300,086 to Gory et al.; 5,944,728 to Bates; 6,331,183 to Suon; and 6,506,209 to Teruo describe various extractors that have a sheath and a grabber comprised of a plurality of catching legs that are unattached at a distal end of the grabber and joined at a proximal base of the grabber. The legs are movable relative to the sheath to achieve a contracted position within the sheath and an extended position outside of the sheath in the form of an open grasper. The distal ends of the legs are farther apart from each other when the grabber is in the open position than when in the closed position. One drawback in the use of grasping forceps is associated with the fact that if the body passage is narrow, it may offer only limited space for the forceps to open and close. Moreover, the catching legs are typically formed of elastic wires with insufficient rigidity to reliably hold the foreign body. Thus, the legs may deform and drop the foreign object during operation.

Another known type of retrieval device is a snare configured as a single distal loop which is positioned over a free end of the foreign body, and which is contracted and tightened around it (see, for example, U.S. Pat. Nos. 1,722,474 to Langbein; 3,828,790 to Curtiss; 4,326,530 to Fleury; 5,171,314 to Dulebohn; 5,171,233 to Amplatz et al.; and 5,417,684 to Jackson et al.).

For example, U.S. Pat. No. 5,171,233 to Amplatz et al. describes a vascular snare that consists of a super-elastic nitinol cable with a single-formed loop. Because of the snare's super elastic construction, the loop can be contracted for passage through a small sheath and yet automatically open into its original, unrestrained configuration upon emerging from the distal tip of the sheath. The loop is formed at approximately 90 degrees to the cable, and this presents the full area of the loop in a distal direction, enhancing the ability to slip the loop over a foreign body and ensnare it by closing the loop with a small sheath. The foreign body is removed from the body passage by withdrawing the device into a guiding catheter. One of the drawbacks of single loop snares is poor cross sectional lumen coverage that requires skilled manipulation to capture the desired object.

In an attempt to provide a snare with improved cross sectional vessel coverage, multi loop snares have been developed. These snares include loops which are joined only at their proximal ends to a manipulation shaft, and otherwise are not joined at any point between the shaft and the distal ends of the loops.

For example, U.S. Pat. No. 5,098,440 to Hillstead describes a method and apparatus for retrieving an object such as a stent from a subject. A catheter supports two wire loops that can be manipulated from outside the subject to engage the object. By manipulating the catheter and the wire loops, the object can be captured and drawn inside a guide catheter through which the catheter is inserted. The catheter and attached stent can then be pulled from the subject.

U.S. Pat. No. 6,099,534 to Bates describes a snare formed of two or more loops. The snare opens and closes for end-entrapping an object and is strengthened by support members that interconnect the loops. The captured object can be released from the snare by opening the loops.

It should be noted that the snares described by Hillstead and Bates include loops which are joined only at their proximal ends to a manipulation shaft, and otherwise are not joined at any point between the shaft and the distal ends of the loops. Such multi-loop snares provide the advantage over single loop snares owing to enhanced cross sectional vessel coverage, and possibility to bring together the free distal ends of the loops and thereby to engage multiple surfaces of an intravascular medical device to be removed. The drawback of the multi-loop snares having loops attached at only the proximal ends is that the relative geometry of the free loops is difficult to maintain due to the lack of dilatative strength. These snares are not resistive to forces countering snare opening. Because the relative position of the loops can change, both within a catheter and within a body tract, the loops can actually become displaced and/or entangled, thus preventing the snare from opening during operation.

This problem is addressed in U.S. Pat. No. 6,458,145 to Ravenscroft et al., which describes an intravascular snare that includes a central shaft with a plurality of loops attached to the shaft at their proximal ends. In order to strengthen the construction, the loops are connected together at joinder points located between the distal and proximal ends of the loops to maintain the relative geometry of the loops in both an expanded and compressed condition. Specifically, each side of each loop in the snare of U.S. Pat. No. 6,458,145 is connected to a side of an adjacent loop at only one joinder point. Although this can strengthen the construction, the structural rigidity and dilatation ability of the snare can still be not sufficient to reliably hold the foreign body.

U.S. Pat. No. 2008/0086149A to Diamant at. al. describes a retrieval snare for entrapping and retaining a foreign object located in a body and a method for manufacturing of the snare are provided. The snare comprises a structure having a proximal portion and a distal portion and includes a plurality of filaments. The filaments extend from an end of the proximal portion towards the distal portion and return to the end of the proximal portion to form a plurality of loops. The loops are not interconnected at the distal portion, but each side of each loop is connected to a side of an adjacent loop in the proximal portion at more than one point, thereby providing structural rigidity and dilatation ability to the snare.

Another known type of technique for removing objects from a body utilizes a suction catheter to a foreign object in a body cavity, for example, to a detached blood clot (thromboembolism) that travels through the bloodstream and lodges so as to obstruct or occlude a blood vessel. The technique involves advancing a suction catheter to the thromboembolism with the goal of removing it via aspiration (i.e. negative pressure).

Many exiting aspiration catheters, for example, export aspiration catheters from Medtronic, pronto extraction catheters manufactured by Vascular Solutions, etc. are all in the form of an aspiration tube, with a dimension sufficient for insertion through a guiding catheter. Thus, the distal tip of such catheters is usually narrow and it does not enable aspiration of large thrombus clots.

For example, U.S. Pat. Appl. Pub. No. US2009/0270808A to Juan-Pablo Mas at. al. describes an aspiration catheter in which rapid withdrawal of a piston disposed within a distal region of a catheter lumen creates a sudden pressure drop for ingestion of intravascular matter into the catheter lumen through a distal port while avoiding large losses of suction common with catheters having long aspiration lumens. One of the disadvantages of this device is associated with the fact that it cannot entrap an object located in a patient's body. Thus, when performing thrombus aspiration, it is not rare that at the end of the aspiration action, and while withdrawing the aspiration catheter, a clot is still attached to the distal tip. The physician is usually not aware of that and can hardly notice this under imaging. This is very dangerous, as the clot can be detached from the catheter and block a normal artery or worse, cause pulmonary or brain embolism. Moreover, such device can be mainly effective with relatively soft thrombus-emboli.

To enhance effectiveness of aspiration techniques, U.S. Pat. Appl. Pub. No. 2006/0058838A to Bose at. al. describes an apparatus for withdrawing thromboembolic material from a blood vessel that includes an aspiration device having an elongate member together with a receiver on a distal portion of the elongate member. The receiver is formed of a plurality of structural members arranged to form a sleeve having a central lumen. A plurality of the structural members comprises engaging elements including apex regions extending into the central lumen. Although the apparatus described in US2006/0058838A provides a possibility to receive a foreign object located in a body, the configuration of the receiver does not allows entrapping and retaining the foreign object within the receiver. Thus, the foreign object can easily escape from the receiver, and the apparatus can drop the object during operation.

SUMMARY OF THE INVENTION

There is a need to provide a convenient and safe retrieval apparatus suitable for reliable and efficient extraction of objects from body tracts. It would also be advantageous to have a retrieval apparatus that can remove objects by a combined action by using aspiration together with grasping. In particular, the apparatus should be able to remove relatively soft objects such as soft blood clots, thrombus clots, occlusions, and small calcinated plaques, urinary stones or stones of the bile duct via aspiration. And if the removal process cannot be completed by suction, the apparatus should be able to accomplish removal of the remaining relatively large objects by mechanical grip of the object and withdrawal it with the entrapping device that seized the object.

It would be advantageous to have a retrieval device that has relatively small dimensions in the undeployed state so it could be easily inserted into the body through known guiding catheters, and then can allow aspiration of relatively large clots/objects, by deployment to a larger dimension.

There is also a need for and would be useful to have a novel aspiration device that would enable aspiration of also large thrombus clots, and also provide a possibility to safely retract the catheter, assuring a clot is attached to the distal tip, by entrapping the clot at the end of the operation.

The present invention satisfies the aforementioned need by providing a retrieval apparatus suitable for entrapping and retaining an object located in a body for its extraction therefrom. The retrieval apparatus includes a snare and a snare control assembly. The snare can change its configuration between a deployed state and contracted state and comprises a structure having a petal shape and including a proximal section and a distal section interconnected to each other. It should be noted that in the description and claims that follow, the terms "proximal" and "distal" are used with reference to the operator of the device. The snare comprises a plurality of filaments extending from a proximal end of the proximal section towards the distal section, and then returning to the proximal end to form a plurality of loops. Segments of the filaments of the distal section are bent with respect to the segments of the filaments of the proximal section such that the retrieval snare in the contracted state forms a hollow cavity extending from the distal section towards the proximal section. Specifically, in the deployed state, the loops are interlaced with each other only within the proximal section, while they are free within the distal section. Distal ends of the loops approach each other when the snare is in the closed state, thereby providing the hollow cavity at the distal section.

According to an embodiment of the present invention, an interlaced pattern of the proximal section is formed by interleaving each lateral side of the filament loop with three corresponding opposite sides of the three neighboring loops arranged in series.

According to an embodiment of the present invention, at least a part of the filament loops are flat and planar along at least a portion of their length. Sides of at least a part of the filament loops are bent within the distal section and arcuate into arcs at a distal end of the distal section to facilitate grasping the captured object.

According to an embodiment of the present invention, the snare control assembly comprises a delivery catheter configured to penetrate into the body for reaching the object and a manipulation member coupled to the snare. The delivery catheter has one or more lumens. The manipulation member is configured to path within at least one lumen of the delivery catheter to operate for (i) protracting the snare from the delivery catheter for opening the snare and (ii) retracting the snare within the delivery catheter for collapsing the retrieval snare inside of the delivery catheter.

According to an embodiment of the present invention, the filaments forming sides of the loops are bent three times to define four straight wire segments angled with respect to each other at a sequence of three angles having predetermined values. For example, the predetermined values of the sequence of three angles counted from the snare proximal end can be in the range of 155-175 degrees, 120-165 degrees, and 95-170 degrees, respectively.

According to an embodiment of the present invention, an opening angle of the loops in a fully deployed state is in the range of about 60 degrees to about 130 degrees.

According to an embodiment of the present invention, the angle between the first and second straight wire segments deviates from the opening angle of the loops in the fully deployed state by about 30 degrees to about 115 degrees.

According to an embodiment of the present invention, the angle between the second and third straight wire segments deviates from the angle between the first and second straight wire segments by 0 to about 50 degrees.

According to an embodiment of the present invention, a relationship between the predetermined values of the sequence of three angles is such that a direction of the third segment counted from the snare proximal end is coaxial with the direction of the delivery catheter.

According to an embodiment of the present invention, a length of the first segment counted from the snare proximal end is greater than the length of the second segment by two to five times.

According to an embodiment of the present invention, a length of the second segment counted from the snare proximal end is equal to or longer than the length of the third segment by up to two times.

According to an embodiment of the present invention, at least one loop has a side that is permanently connected along the proximal portion to an opposite side of an adjacent loop at more than one connection point. For example, the permanent connection can be carried out by twisting each pair of the filaments.

According to an embodiment of the present invention, each side of each loop is permanently connected to a side of an adjacent loop near the proximal end along a predetermined segment length.

According to an embodiment of the present invention, the loops are permanently interconnected to each other at least at one additional joint point selected within the proximal section in places where one loop crosses another loop.

According to an embodiment of the present invention, a part of the filament loops are made of a thicker wire than the wire of the remaining loops.

According to an embodiment of the present invention, a part of the loops have dimensions and shapes different from the dimensions and shapes of the other loops.

According to one embodiment of the present invention, the snare also includes a mesh formed by interweaved and/or overlapping wires weaved around a snare carcass structure formed by the filaments.

According to another embodiment of the present invention, the snare also includes a cover film configured for coating a snare carcass structure formed by the filaments.

According to a further embodiment of the present invention, the cover film is made from silicon, polyurethane, PTFE, TEFLON etc.

According to another embodiment of the present invention, the cover film has radiopaque properties.

According to another embodiment of the present invention, the cover film has one or more holes of a predetermined size, e.g., between 5 micron and 200 microns (or even greater) for the passage of blood flow when the device is in a blood vessel.

According to a further embodiment of the present invention, the snare also includes a closing element that is arranged at a distal section and configured for binding the loops together at their distal ends.

According to one embodiment of the present invention, the manipulation member includes at least a part of the plurality of filaments extending from the snare proximal end.

According to another embodiment of the present invention, the manipulation member includes a pushing tube containing at least a part of the plurality of filaments axially disposed within a lumen of the pushing tube along at least a portion of the tube's length.

According to a further embodiment of the present invention, the manipulation member includes an aspiration tube coupled to the filament loops at the proximal end of the snare along an external surface circumference of the aspiration tube. The device of this embodiment is designed to remove various organic units of the hollow organs, due to aspiration through a channel formed by a lumen in the aspiration tube.

According to still another embodiment of the present invention, the manipulation member includes an aspiration lumen and a guide wire lumen, both lumens extending between the proximal and distal ends of the manipulation member.

According to an embodiment of the present invention, the wire guide lumen is arranged within the aspiration lumen and separated from the aspiration lumen by a separation wall.

According to an embodiment of the present invention, the delivery catheter includes a snare lumen and a guide wire lumen, both lumens extending between the proximal and distal ends of the delivery catheter.

According to one embodiment of the present invention, the retrieval apparatus further comprises a guiding catheter including a lumen configured for housing the delivery catheter, a guide wire extending within the guide wire lumen; and a suction device coupled to the aspiration lumen at the proximal end of the manipulation member.

According to another embodiment of the present invention, the retrieval apparatus further comprises a guiding catheter including a lumen configured for housing the delivery catheter, a guide wire extending within the guide wire lumen; and a suction device coupled to the aspiration lumen at the proximal end of the delivery catheter.

According to one embodiment of the invention, the filaments are made of non-metallic material. Examples of the non-metallic material include, but are not limited to, Capron, Nylon, etc.

According to another embodiment of the invention, the filaments are made of metallic material. The metallic material can have a thermo-mechanical shape memory characteristic. Moreover, the metallic material can have a superelastic characteristic. Examples of the metallic material include, but are not limited to NiTi based alloy and stainless steel.

When desired, the metallic material includes a material which provides radiopacity. For example, the material which provides radiopacity is a noble metal. Likewise, the metallic material can be alloyed with one or more of the following metals: palladium (Pd), tungsten (W), niobium (Nb), cobalt (Co), gold (Au), silver (Ag), tantalum (Ta) and copper (Cu).

According to one embodiment of the invention, the filaments are made of a core tube (cannular strand) containing an axially disposed radiopaque wire.

According to another embodiment of the invention, the filaments are covered by a coating layer. Preferably, but not mandatory, the coating layer is made of a radiopaque material.

According to a further embodiment of the invention, the retrieval apparatus can include at least one radiopaque marker attached to at least one loop in said distal portion. For example, the radiopaque marker is a ferrule placed around the filament.

According to one embodiment of the invention, the filaments are single-core wires.

According to another embodiment of the invention, the filaments are multiwire strands. For example, the multiwire strands can include a central core wire and at least one other wire twisted about said central core wire. Such an other wire can, for example, be made of a material having a level of radiopacity greater than the level of radiopacity of the central core wire. For example, such another wire can be made of or include one or more of the following metals: Pt, Au, Pd, W, Nb, Co, Ag, and Cu.

According to still a further embodiment of the invention, the device is an aspiration device comprised of a snare attached to an aspiration catheter. The snare can be in a contracted form while delivered to the clot site, thus enabling easy delivery through known guiding catheters, and when delivered to the clot site, it is deployed to the full size of the vessel, thus enabling aspiration of large clots. When aspiration action is finalized, the snare part is closed in a manner it entraps remaining clot and thus the catheter could be retraced safely, without risk of clot shift and embolism. Such a device can be used, but not limited to, coronary thrombus aspiration, peripherals thrombus aspiration, pulmonary embolism aspiration, and other application of thrombus aspiration.

There has thus been outlined, rather broadly, the more important features of the invention in order that the detailed description thereof that follows hereinafter may be better understood. Additional details and advantages of the invention will be set forth in the detailed description, and in part will be appreciated from the description, or may be learned by practice of the invention.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 1A and 1B illustrate a cross-sectional plan view and a top view, respectively, of a distal portion of a retrieval apparatus for entrapping and retaining an object in a deployed position, according to one embodiment of the present invention;

DETAILED DESCRIPTION OF EMBODIMENTS

Figure 1C:
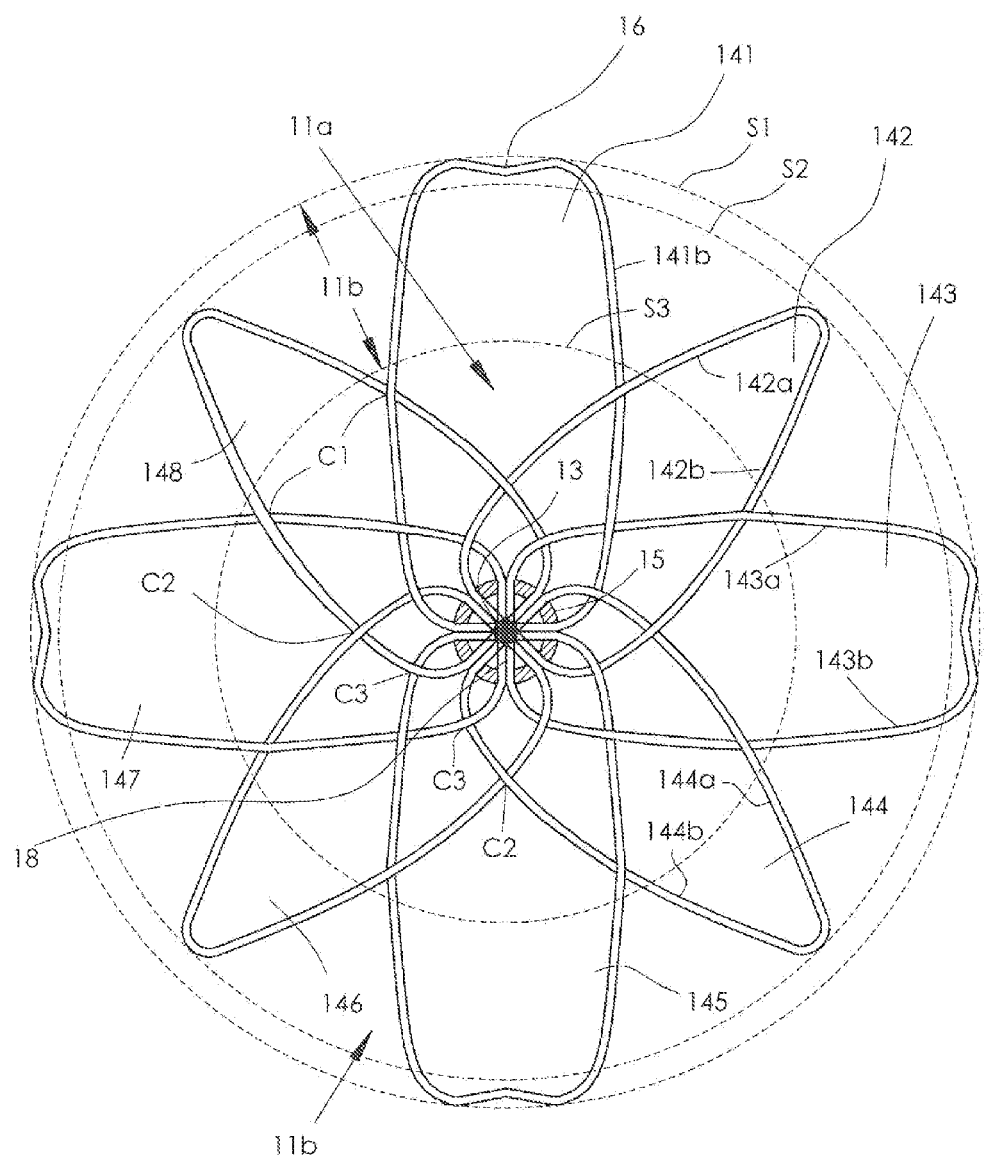
FIG. 1C illustrates a pattern of interlacing filaments at a distal portion of the retrieval apparatus in a deployed position of the embodiment shown in FIG. 1B.

The principles of the method for the medical device according to the present invention may be better understood with reference to the drawings and the accompanying description, wherein like reference numerals have been used throughout to designate identical elements. It being understood that these drawings which are not necessarily to scale, are given for illustrative purposes only and are not intended to limit the scope of the invention. Examples of constructions, materials, dimensions, and manufacturing processes are provided for selected elements. Those versed in the art should appreciate that many of the examples provided have suitable alternatives which may be utilized.

Embodiments of the present invention generally provide a retrieval apparatus that includes a retrieval snare including a central structure with a plurality of filament loops at a distal part of the apparatus, and a snare control assembly coupled to the snare structure. The snare control assembly includes a delivery catheter configured to penetrate into the body for reaching the object; and a manipulation member coupled to the snare. The manipulation member is configured to path within the delivery catheter and to operate for (i) protracting the snare from the delivery catheter for opening the snare, and (ii) retracting the snare within the delivery catheter for collapsing the retrieval snare inside of the delivery catheter.

FIGS. 1A and 1B illustrate cross-sectional plan and top views, respectively, of the distal part of a retrieval apparatus 10 with the snare 11 in a deployed position for entrapping and retaining an object, according to one embodiment of the present invention. The cross-sectional plan view in FIG. 1A is taken along line C-C in FIG. 1B.

The retrieval apparatus 10 includes the snare 11 and a snare control assembly 19 coupled to the snare 11. The snare control assembly 19 includes a manipulation member 17 coupled to a snare proximal end 13 as will be described in detail hereinbelow, and a delivery catheter 15. The delivery catheter 15 is a thin-walled, cylindrical deflectable tube fabricated of a relatively stiff yet somewhat pliant material, which operates as a sheath and permits the apparatus to be introduced into a patient's body along a tortuous path for reaching an object. For example, the delivery catheter 15 can be made of polymeric material, such as polyimide, polyvinyl chloride, NYLON, TEFLON, etc. The delivery catheter 15 can also be made of metal or composite materials. For example, it can be made in the form of a coil, (e.g., stainless steel coil) or a metal tube. When desired, the sheath 15 may be multi-layered with different materials in order to provide a graduated bending and stiffness characteristic over its length.

The structure of the retrieval snare 11 comprises a proximal section 11a and a distal section 11b and is formed by a plurality of filaments that extend from a proximal end 13 of the proximal portion 11a towards the distal section 11b and then return to the proximal end 13 to form a plurality of filament loops 14 and 140 each loop having two opposite lateral sides 14a (left loop side in FIG. 1A) and 14b (right loop side in FIG. 1A). Such a structure has a petal shape and comprises two or more petals formed by the filament loops 14. The structure of the retrieval snare 11 can have an open petal shape and a closed petal shape. When the structure has an open petal shape, the loops 14 and 140 are arranged radially outward and away from each other in the distal section 11b. The open state of the retrieval snare 11 is achieved when the snare is deployed outside of the dilator catheter 15. However, when the dilator catheter 15 runs over the petal loops 14 and 140, distal ends of the loops approach each other and come together. The snare can reach a closed state when an opening at the distal end of the snare 11 is closed, as will be described hereinbelow.

Figure 2A:
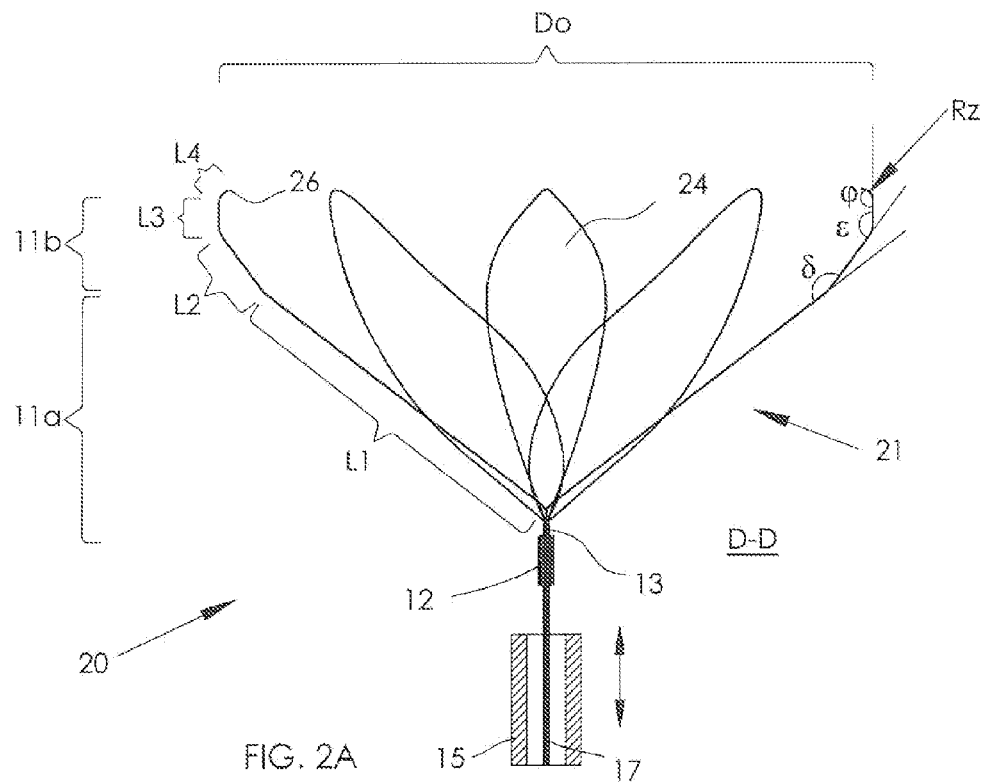
FIGS. 2A and 2B illustrate a cross-sectional plan and a top view, respectively, of a retrieval apparatus in a deployed position, according to another embodiment of the present invention.
Figure 2B:
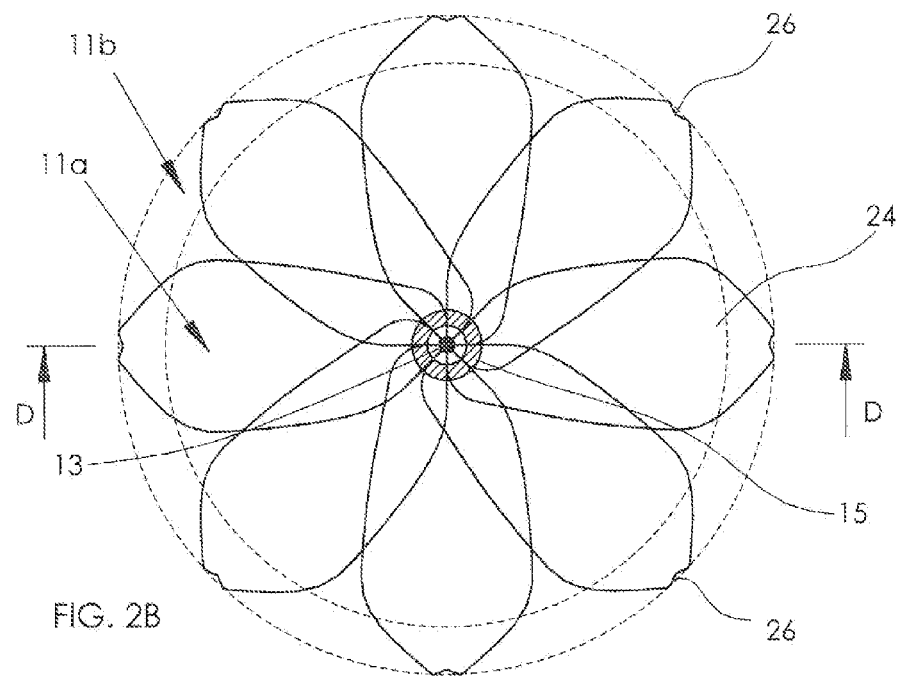

The filament loops can, for example, all be of the same dimension and shape (as shown in FIGS. 2A and 2B). Alternatively, at least a part of the filament loops may have dimensions and shapes different from the dimensions and shapes of the other loops. For example, two types of filament loops, such as the filament loops 14 and the filament loops 140 are shown in FIG. 1A and FIG. 1B, although other configurations of the filament loops are also contemplated. A dotted circle S1 has a diameter $D_0$ and shows a dimension of the loops 14, whereas a dotted circle S2 has a diameter $D_C$ and shows a dimension of the loops 140.

Moreover, the filament loops 14 can be either symmetric or asymmetric. For example, each of the loops 14 and 140 shown in FIG. 1A and FIG. 1B is axially symmetric with respect to the axis passing through the proximal end 13.

In the proximal portion 11a, the filament loops overlap and/or interlace. Note that the term "overlap" herein is broadly used to describe such arrangement of the filaments, in which one element crosses other filaments, i.e., one of the filaments always being over or under the other filaments. The term "interlace" herein is broadly used to describe the situation when at least one filament interweaves with the other filaments, i.e., one of the filaments passes first above the crossed filament and then passes under the next crossed filament.

According to the embodiment shown in FIGS. 1A and 1B, the structure of the retrieval snare 11 has an eight petals shape, where the filament loops 14 have two types of dimensions and symmetric shapes, which alternate one after another. An interlaced pattern of the proximal section 11a is formed by interleaving each lateral side 14b of the loop 14 with three corresponding opposite sides 14a of the three neighboring loops arranged in series in clockwise direction (in places C1, C2 and C3, correspondingly, where one loop crosses another loop without "permanent" link), or vice versa, by interleaving each side 14a of the loop 14 with three opposite sides 14b of the three neighboring loops arranged in series in counter-clockwise direction, so as to define a net. This feature provides desired structural rigidity and dilatation ability to the retrieval apparatus 10.

Specifically, the interlaced pattern described above is shown in FIG. 1C. The snare structure comprises two types of loops. Loops 141, 142, 145 and 147 are longer than loops 142, 144, 146 and 148. A side 141b of the loop 141 first passes under the crossed filament of the side 142a of the adjacent loop 142 in places C1 at a distal end (indicated by a dotted circle S3) of the proximal section 11a, then it passes above the crossed filament of a side 143a of the loop 143 in places C2, and finally it passes again under the crossed filament of the side 144a of the adjacent loop 144 in places C3 near the proximal end 13. Likewise, in the counterclockwise direction, a side 141a of a loop 141 first passes above the crossed filament of the side 142b of the adjacent loop 142 at the distal end S3 of the proximal portion 11a, then it passes under the crossed filament of a side 143b of the loop 143, and finally it passes again above the crossed filament of the side 144b of the adjacent loop 144 near the proximal end (13 in FIG. 1A) of the proximal portion 11a. The rest of the filament loops are arranged similarly.

According to the embodiment shown in FIGS. 1A-1C, each side of each loop is adjacent to a side of a diametrically opposite loop near the proximal end 13 along a segment 18 from the proximal end 13 along a predetermined segment length. Such a predetermined segment length can, for example, be the length corresponding to the inner radius of the delivery catheter 15, although other values for the length are also contemplated.

However, when desired, each side of each loop can be "permanently" connected to a side of a diametrically opposite loop near the proximal end 13. The connection may extend along at least a portion of the segment 18 from the proximal end 13 along the predetermined segment length. The loop sides can, for example, be connected along the segment 18 by twisting each pair filaments forming the corresponding sides together by one or more turns. When desired, the permanent connection of the adjacent filaments can be archived by soldering, brazing, welding gluing, etc.

Referring to FIGS. 1A, 1B and 1C together, the filament loops 14 and 140 of the snare 11 are not interconnected in the distal section 11b. Specifically, the loops 14 and 140 deploy radially outward and away from each other in the distal section 11b when the snare 11 is deployed outside the delivery catheter 15.

Attention is now drawn to the configuration of the filament loops 14 and 140 themselves. According to the embodiment shown in FIGS. 1A-1C, half of the filament loops (i.e., the loops 14 in FIGS. 1A and 1B and the loops 141, 142, 145 and 147 in FIG. 1C) has a length longer than the other half of the filament loops (i.e., the loops 140 in FIGS. 1A and 1B and the loops 142, 144, 146 and 148 in FIG. 1C).

All the loops are flat and planar along the length of the first half, whereas then the sides of these filament loops are slightly bent within the distal section 11b. Moreover, the longer loops (i.e., the loops 14 in FIGS. 1A and 1B and the loops 141, 142, 145 and 147 in FIG. 1C) also arcuate into arcs 16 at the end of the distal section 11b to facilitate grasping the captured object. A curvature radius $R_z$ of arcs 16 and the entire dimension of the arcs 16 depend on the dimension of the snare. For example, $R_z$ can be in the range of 1-3 mm, whereas the entire dimension of the arcs 16 can, for example, be in the range of 0.2 mm-6 mm. In particular, for the snare having the length of 5 cm and the diameter $D_0$ of 5 cm, the curvature radius $R_z$ can be 5 mm.

According to an embodiment of the present invention, the filaments of the loops forming sides 14a and 14b can be gradually bent one or more times to define straight wire segments angled with respect to each other, although a continuously bent arc having C-shaped configuration of the sides 14a and 14b at the distal section 11b can also be contemplated. In the example shown in FIG. 1A, the filaments of the loops 14 are bent three times to define straight wire segments $L_1$, $L_2$, $L_3$ and $L_4$ angled with respect to each other at angle $\delta$ between the wire segments $L_1$ and $L_2$; at angle $\epsilon$ between the wire segments $L_2$ and $L_3$; and at angle $\phi$ between the wire segments $L_3$ and $L_4$, respectively.

Figure 15A:
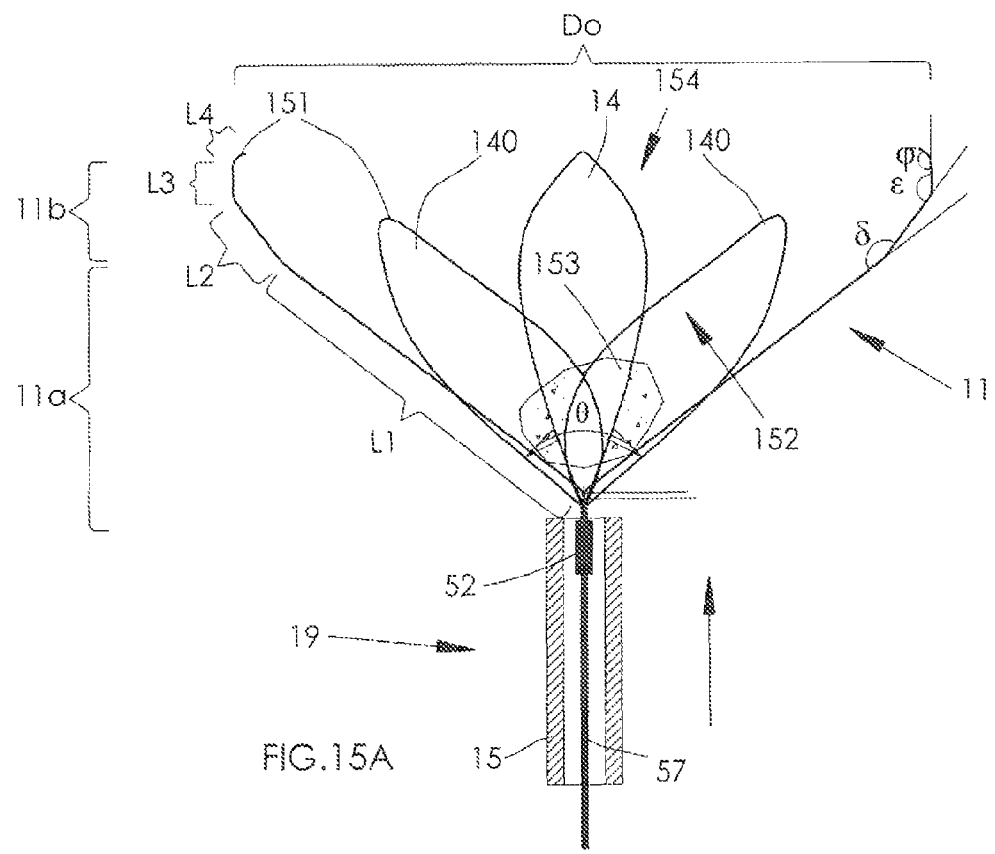
FIG. 15A illustrates a schematic longitudinal cross-sectional view the retrieval apparatus shown in FIGS. 1A and 1B in a partially contracted position when the snare is partially retracted in a delivery catheter.
Figure 15B:
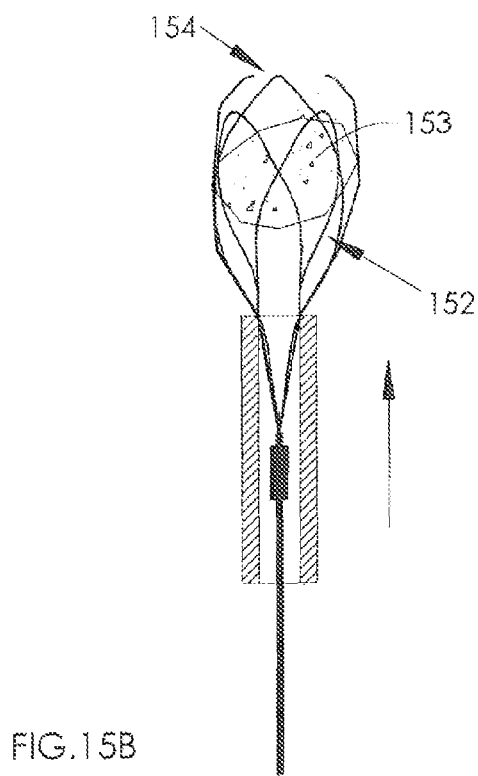
FIG. 15B illustrates the snare shown in FIG. 15A during a further retraction in the delivery catheter.

Referring to FIGS. 15A and 15B together, when the delivery catheter 15 comes over to the snare 11 or when the snare is retracted into the delivery catheter 15, distal ends 151 of the loops 14 can come together, thereby forming a hollow cavity 152 of the snare 11. The cavity 152 formed by the loops 14 can extend between the distal section and the proximal section of the snare. In operation, the loops 14 and 140 can slip over a foreign object (e.g., stone, blood clot, plaque, etc.) 153 and catch it. When the object 153 comes inside the cavity 152 of the snare 11, the delivery catheter 15 (controlled by a manipulator (not shown) included into the snare control assembly) runs over the petal loops 14 and 140 of the snare 11. In this case, the snare 11 starts to collapse, while remaining at the same location. Since an inner diameter of the delivery catheter 15 is significantly smaller than the maximal diameter $D_0$ of the snare 11 in a deployed state, the loops 14 and 140 change an opening angle $\theta$, and the object 153 becomes entrapped. Moreover, the arcs 16 formed at the ends of the loops 14 can work as teeth that facilitate grasping the captured object.

In the beginning of operation, the distal section 11b of the snare 11 does not change its configuration, and the angles $\delta$, $\epsilon$, $\phi$ remain the same values. If a dimension of the object 153 is less than the dimension of the snare cavity 152, a further forward movement of the delivery catheter 15 can result in approaching the distal ends 151 of the loops 14 together, as shown in FIG. 15B, and thereby closing of an opening 154 at the distal end of the snare 11. In such a case, the loops 14 ensnare the object 153 within the hollow cavity 152 without squeezing. It should be noted that owing to the specific configuration of the angles $\delta$, $\epsilon$, $\phi$, when the snare 11 is in the closed state, the hollow snare cavity 152 is still not fully contracted and maintains a certain volume (even without foreign objects within the cavity).

When a dimension of the object 153 is smaller than the inner diameter of the delivery catheter 15, the snare can arrive inside the delivery catheter 15 together with the object. It can happen in the case when the delivery catheter 15 reaches the transition region between wire segments L1 and L2 due to elastic deformation of petals and changing the angle $\delta$.

Alternatively, when a dimension of the object 153 is greater than the hollow cavity 152, to the gradually bent loops 14 and 140 can capture and grasp the object without pushing it out owing to the specific configuration of the angles $\delta$, $\epsilon$, $\phi$. Moreover, the captured object can be removed from the hollow organs together with the snare 11.

In order that the proposed device would work properly, it is necessary that several conditions are met. Specifically, the angles $\delta$, $\epsilon$, $\phi$ should have certain values. Preferably, the angle $\delta$ can be in the range of 160° to 175'; the angle $\epsilon$ can be in the range of 125° to 165°; and the angle $\phi$ can be in the range of 95° to 170°. Meanwhile, the angle $\delta$ should always be equal to or greater than $\epsilon$, and these angles are related by the following relationship $\delta \approx \epsilon + \Delta 1$, where $\Delta 1$ is in the range of 0° to 50°.

Furthermore, the opening angle $\theta$ of the fully deployed snare is in the range of about 60 degrees to about 130 degrees. The effective value of the opening angle $\theta$ depends on the snare application, and is mainly determined by the size of the foreign object. Furthermore, the angle between the two first straight wire segments L1 and L2 deviates from the opening angle $\theta$ of the loops in the fully deployed state by a predetermined value. Thus, the angles $\theta$ and $\delta$ should be linked together, i.e., $\delta \approx \theta + \Delta 2$, where $\Delta 2$ is in the range of 30° to 115°. Moreover, a relationship between the angles $\delta$, $\epsilon$, $\phi$ and $\theta$ is preferably such that a direction of the segment L3 is coaxial with the direction of the delivery catheter 15.

In addition, a length of L1 must be greater than the length L2, preferably by two to six times. Furthermore, the segment L2 must be equal to or longer than the segment L3 by up to two times. For example, for a snare of the size of 6×6 mm, the length of the segment L1 can be in the range of 4 mm to 7 mm; the segment L2 can be in the range of 0.7 mm to 3 mm; the segment L3 can be in the range of 0.3 mm to 1 mm; and the length of the segment L4 may be in the range 0.2 mm to 1 mm. Preferably, but not mandatory, the dimensions of a 6×6 mm snare can be set to: L1≈5.5 mm; L2≈1.5 mm; L3≈0.4 mm and L4≈0.3 mm. The actual characteristics of the snare depend on the application of the retrieval apparatus and whether it is intended to operate in a bladder, kidney or blood vessel.

According to an embodiment, the filament loops 14 and 140 of the snare are made from wires of the same diameter. When desired, a part of the loops 14 and 140 can be made of a relatively thicker wire than other loops. For example, in a snare structure with an even number of petal loops, half of the loops can be made of a thicker wire, which thus act as force elements (for example, the loops 14), to bear the brunt in the capture of the objects, whereas the remaining loops (for example, the loops 140) can be made of a thinner wire, and thereby they can perform a supporting function, since they can overlap the space between the force loop elements, and thereby securely hold small objects within the snare. Moreover, the use of wires of different diameters reduces the diameter of the closed snare, and enables usage of a catheter with a smaller diameter. This feature is especially important when the retrieval apparatus is used in hollow organs of small diameter, for example in blood vessels. The presence of wires of different diameters facilitates the deformation of the petals at the entrance to the delivery catheter 15 and enables production of apparatuses with different diameters in the closed position starting from 1 Fr (0.33 mm) and greater.

Each filament of the snares shown in FIGS. 1A-1C is a single-core wire. According to another embodiment of the invention, each filament is a multi-wire strand or multi-core wire. The filaments of the retrieval basket 11 can each have a cross-sectional diameter in the range of about 0.05 mm to about 0.3 mm. The diameters of the filaments may vary from wire-to-wire and/or along the lengths of each wire.

The filaments utilized for the fabrication of the retrieval snare 11 are made of a suitable material that is suitably biocompatible and has thermo-mechanical shape memory and/or superelastic properties. According to one embodiment of the invention, the filaments are made of a metallic material. For example, the metallic material can be selected from a group including a NiTi based alloy (e.g., Nitinol), stainless steel and other materials possessing good shape memory, elastic or superelastic characteristics. According to another embodiment of the invention, the filaments are made of non-metallic material, for example Capron, Nylon, etc.

According to a still further embodiment of the invention, the filaments of the snare are covered by an insulating layer. The insulating layer can, for example, be made of Teflon. The advantage of Teflon is its thermal resistance and low coefficient of mechanical friction, which leads to an additional reduction of traumatism.

According to a still further embodiment of the invention, the filaments of the snare can be covered by hydrophilic coating which also provides a value of the friction coefficient.

A preferable, but not mandatory feature is, the filaments being radiopaque, so as to permit them to be visualized by a fluoroscope with respect to the object to be retracted. Thus, according to one example, radiopacity may be provided by the metallic material from which the filaments are made and may include a material which provides radiopacity, for example a noble metal, such as gold, tantalum, platinum, etc. Likewise, the metallic material can be alloyed with one or more of the following metals: Pd, W, Nb, Co, and Cu.

According to another example, the filaments are made of a core tube (cannular strand) containing an axially disposed radiopaque wire, for example, a radiopaque core clad with a different outer material. Examples of radiopaque materials include Pt, Au, Pd, W, Nb, Co, Ta, Ag, and Cu without limitation. Examples of cladding materials include stainless steel, Nitinol, and polymers such as Capron and Nylon without limitation.

According to yet another example, the filaments can have radiopaque parts of a predetermined length. These radiopaque parts can form the distal portion 11b of the snare or at least a part of the distal portion.

Radiopacity can also be improved through coating processes such as sputtering or plating a radiopaque material onto the filaments, or the snare being fabricated from these filaments, thereby to provide a radiopaque coating layer on the filaments.

Likewise, radiopacity can yet be improved by using radiopaque markers (not shown), which can be attached to or placed around the filaments forming the snare. In this manner, materials which have higher radiopacity than the snare structure itself, such as gold, tantalum or platinum, can be utilized as markers and be strategically placed along the body of the snare to increase the visualization of the snare. For example, the retrieval snare 11 can comprise one or more radiopaque markers (not shown) attached to or placed around the filaments forming one or more loops in the distal section 11b. For example, the radiopaque marker can be a ferrule put on the filament.

According to another embodiment of the invention, the filaments can be multi-wire strands. In such a case, in order to improve radiopacity, the multi-wire strands can include a central core wire and at least one another wire twisted about the central core wire which is made of a material having a level of radiopacity greater than the level of radiopacity of the central core wire. Examples of such a material include, but are not limited to, Pt, Au, Pd, Ag, Ta, etc.

Referring to FIGS. 2A and 2B together, cross-sectional plan and top views, respectively, of the distal part of a retrieval apparatus 20 with a snare 21 in a deployed position for entrapping and retaining an object are illustrated, according to another embodiment of the present invention. The cross-sectional plan view in FIG. 2A is taken along line D-D in FIG. 2B. The snare 21 differs from the snare 11 shown in FIGS. 1A-1C in the fact that all filament loops 24 of the snare 21 have the same length, and are slightly bent and arcuate at the end of the distal section 21b to form grabbing teeth 26 (similar to the grabbing teeth (16 in FIG. 1B). It should be understood that the teeth 26 can only be formed on a part of the loops 24.

Moreover, as can be seen in FIG. 2B, the filament loops 24 have asymmetrical shape near the proximal end 13 of the proximal section 21a of the snare 21. Such asymmetrical shape of the loops near the proximal end provides additional radial stability when closing or opening the snare for grabbing and removing concretions.

Figure 3:
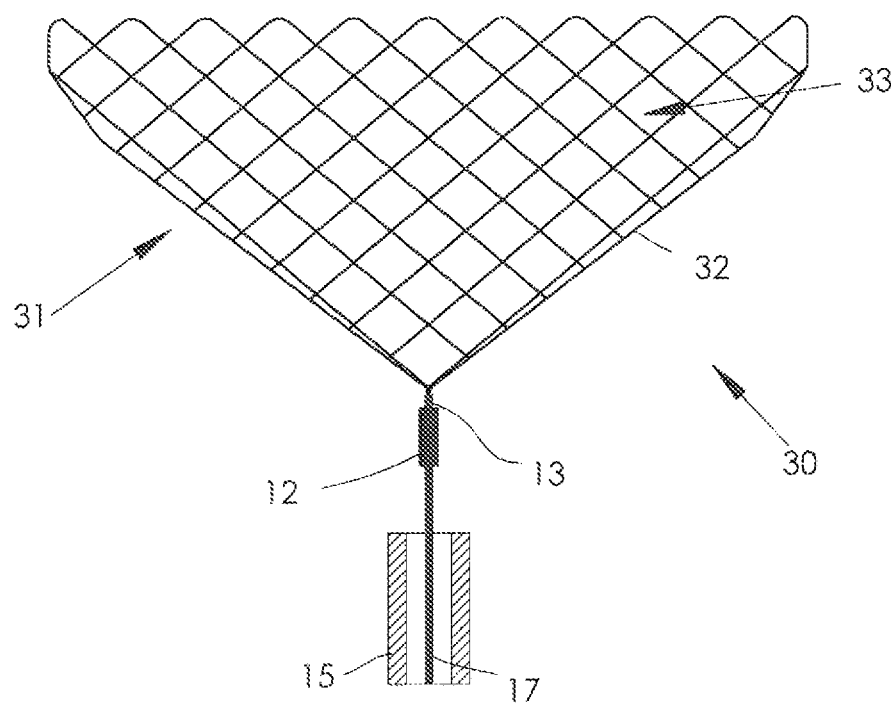
FIGS. 3, 4, 5A and 5B illustrate a plan view of the distal part of a retrieval apparatus in a deployed position with various snares according to several further embodiments of the present invention.

Referring to FIG. 3, a plan view of the distal part of a retrieval apparatus 30 with a snare 31 in a deployed position for entrapping and retaining an object (not shown) is illustrated, according to still another embodiment of the present invention. The snare 30 generally includes a snare carcass structure 32 formed of filament loops (14 and 140 in FIG. 1A or 24 in FIG. 2A) and a mesh 33 weaved around the carcass structure 32 formed by interweaved and/or overlapping wires. The mesh 33 can, for example, be formed from suitable metallic or polymeric wires having a thinner diameter than the diameter of the wires of the filament loops. This apparatus, as in the previous cases, is formed from loops having filaments angled at different angles along their length, and it operates according to the principle described above. It should be understood that using the cellular structure of the snare 31 can make the cell structure more dense, which allows capturing smaller formations.

Figure 4:
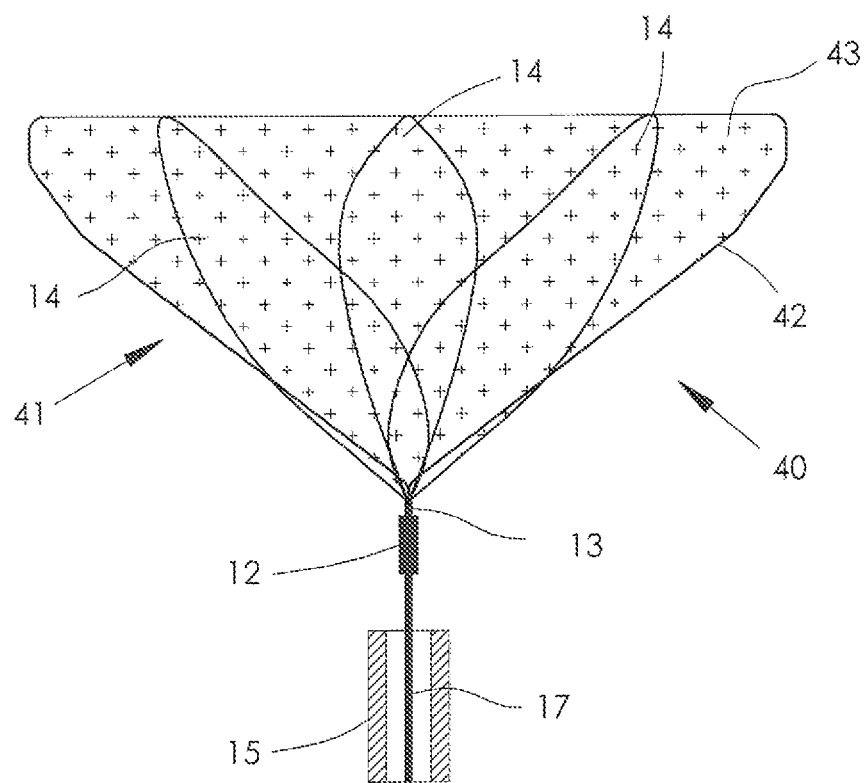

Referring to FIG. 4, a plan view of the distal part of a retrieval apparatus 40 with a snare 41 in a deployed position for entrapping and retaining an object (not shown) is illustrated, according to a further embodiment of the present invention. The snare 40 generally includes a snare carcass structure 42 formed of the filaments and a cover film 43 configured for coating the carcass structure 42. The term "coating" here has a broad meaning. Thus, according to one embodiment, the cover film 43 is attached to the carcass structure 42 from outside of the carcass structure 42 and wrapping thereof. According to another embodiment, the cover film 43 is attached to the carcass structure 42 from inside of the carcass structure 42. Likewise, the carcass structure 42 can be embedded into the cover film 43. The cover film 43 can for example, be made of polyurethane, polyester, TEFLON, PTFE, organosilicic materials, etc. The snare 41 can be most useful when a clinician wants to remove gelatinous organic-education, such as blood clots. By using the aspiration tube, a clinician may withdraw thromboembolic material or some other small inclusions inside of hollow organs The cover film 43 can be completely impenetrable or have one or more holes of a predetermined size, e.g., between 5 micron and 200 microns (or even greater) for the passage of blood flow when the device is in a blood vessel.

Methods for coating the carcass 42 with a cover film may be very different, such as gluing the film to the wire, placing the film to the wires from the solution, the growing film directly on the wires by immersing the device in a special solution, melting polymeric films around the wires, etc. The thickness of the polymeric film 43 coating the wires should be chosen appropriately in order to retain the captured formation without obstruction of the operation of the retrieval apparatus 40. The coating also must have a minimal coefficient of friction. Low coefficient of friction will allow the snare to move freely within the catheter 15 during deploying and collapsing the snare 41. To meet these requirements, the cover film 43 can be laminated and formed from layers with different properties. For example, the first layer may be applied to improve adhesion of the functional coating, whereas the upper layer can be a hydrophilic coating to reduce friction.

Figure 5A:
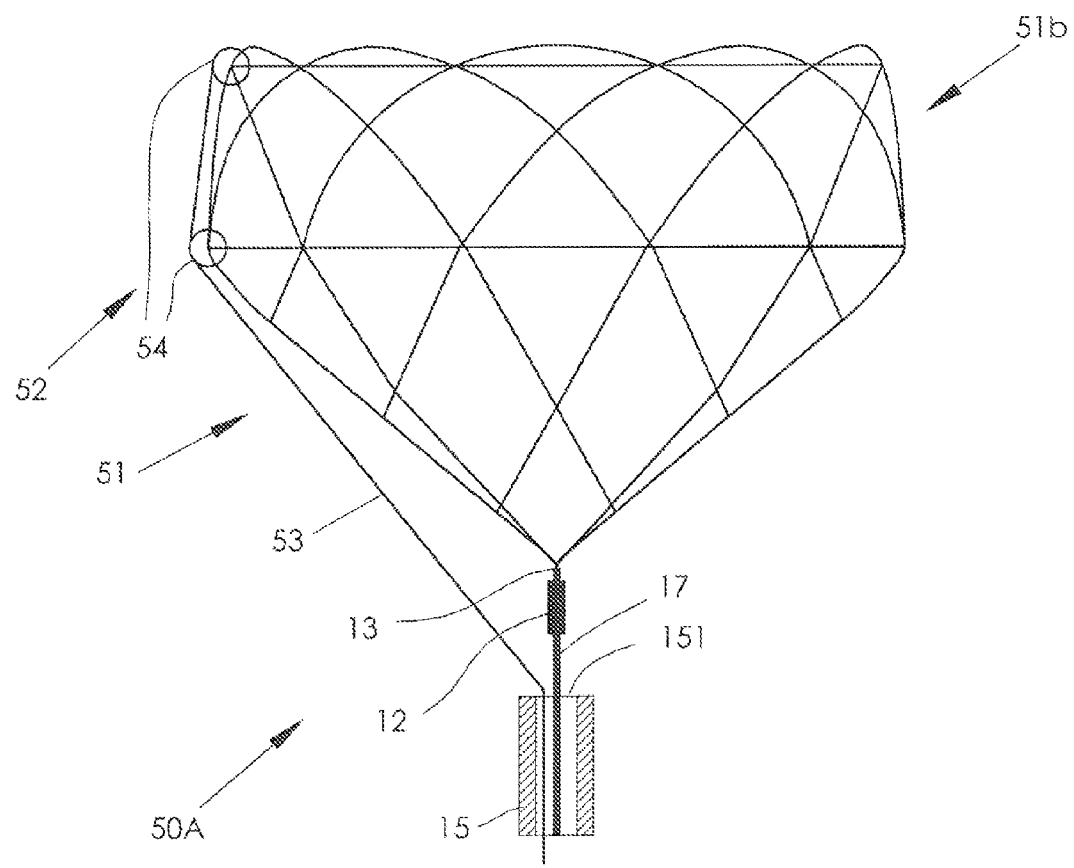
Figure 5B:
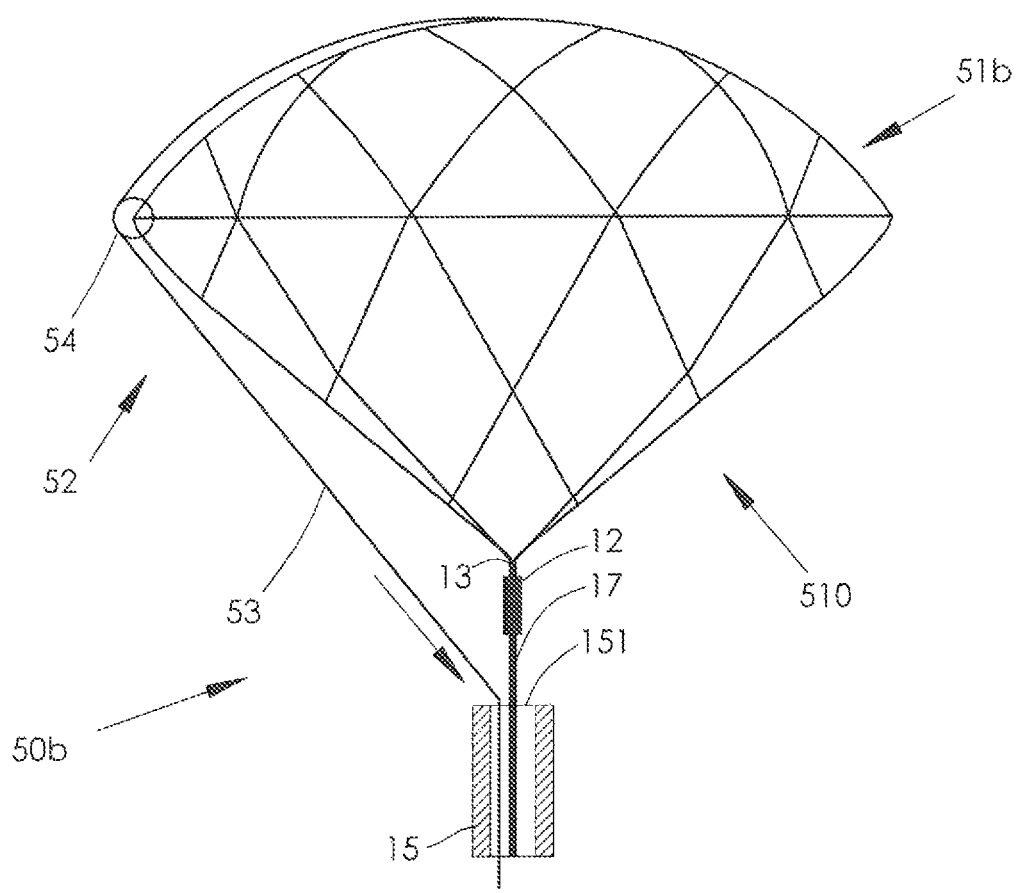

Referring to FIGS. 5A and 5B, plan views of the distal part of a retrieval apparatus 50A and apparatus 50B with a snare 51 and a snare 510, correspondingly, in a deployed position for entrapping and retaining an object (not shown) are illustrated, according to still a further embodiment of the present invention. The snares 51 and 510 differ from the snare (11 in FIGS. 1A and 1B) and from the snare (21 in FIGS. 2A and 2B) in the fact that snares 51 and 510 further include a closing element 52 that is arranged at a distal section 51b configured for binding the loops together at their distal ends, thereby closing the snares 51 and 510.

According to an embodiment, the closing element 52 includes a control thread 53 and one or more rings 54 arranged on the filaments of the snares 51 and 510 along their circumferences in the distal section 51b. The control thread 53 then passes through the rings 54, and further extends through a lumen 151 of the delivery catheter 15. In operation, in order to entrap the captured object, the control thread 53 may be pulled in the management of the manipulation member 17 toward the proximal end of the retrieval apparatus, which results in tightening the filament loops, and thereby closing the snare at the distal end.

Referring to FIGS. 1A through 5B together, the filaments are bound together at the end 13 of the proximal section. According to an embodiment of the invention, the filaments are bound together by a first ferrule 12 crimped or swaged together with the filaments at the end 13 of the proximal portion. The filaments that extend from the ferrule 12 can be bound together, for example, by twisting together. Thus, these twisted filaments can possess sufficient stiffness in order to form or be a part of a manipulation member 17 of the retrieval apparatus 10. The manipulation member 17 is arranged within the delivery catheter 15 and is operable for retracting the snare within the sheath 15 and protracting the snare therefrom for its opening. The manipulation member 17 connects the snare (11, 21, 31, 41, 51A and 51B) to a manipulator (not shown) that is operable for manipulating the snare for extraction of the object from the body. When desired, the manipulation member 17 can be formed from at least a part of the plurality of filaments extending from the end 13 towards the manipulator.

In practice, an operator of the snare can manipulate the manipulation member 17 by means of the manipulator, and thus the snare can be either retracted within the catheter 15 or protracted therefrom. The operator, by holding the manipulator, can also maneuver the catheter 15 within the body organ (not shown), (e.g. to displace it by turning, pushing or pulling).

Figure 6:
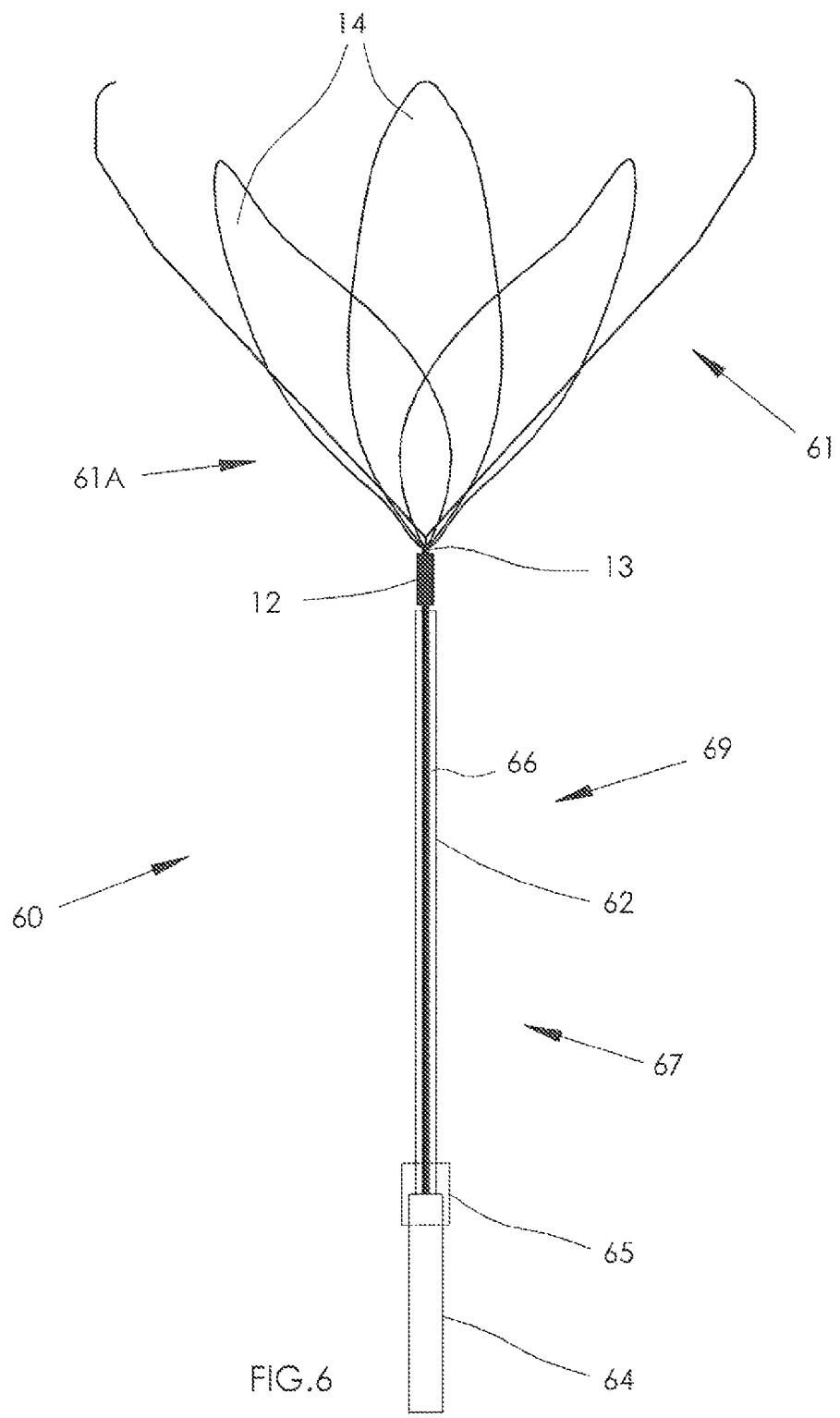
FIG. 6 illustrates a schematic view of connection of the loops of the retrieval snare shown in FIGS. 1A, 2A, 3, 4, 5A and 5B to a manipulation member, according to one embodiment of the invention.

Referring to FIG. 6, a retrieval snare apparatus 60 is shown which includes any one of the snares 61 described above and the snare control assembly 69. The snare control assembly 69 includes a manipulation member 67 having a pushing tube 62 and a manipulator 64 connected to the tube 62. At least a part of the filaments 66 bound together at the end 13 and extend further from the end 13 towards the manipulator 64. When desired, the filaments can be twisted together to provide additional rigidity to the manipulation member. These filaments 66 are axially disposed within a lumen of the tube 62 along at least a portion of the tube's length. The tube 62 and the filaments 66 can be bound together. For example, the tube 62 and the filaments 66 can be crimped, swaged, glued, soldered or welded together. When desired to increase the surface area binding the filaments to the tube, the tube 62 can have one or more notches (not shown) through which a glue or soldering material can be delivered.

In some embodiments, the tube 62 may be disposed within the delivery catheter (not shown in FIG. 6) as described above. In another embodiment, the tube 62 may be arranged between the first ferrule 12 and the manipulator 64, as shown in FIG. 6. Alternatively, the tube 62 can bind together the filaments at the end 13 of the proximal section 61A of the snare 61, essentially functioning as the first ferrule 12, and thereby allowing the ferrule 12 to be omitted.

The tube 62 can, for example, be made of a metallic material selected from a NiTi based alloy, or stainless steel. Likewise, the tube 62 can be made of a polymer material. According to one example, the manipulation member 67 can be connected to the manipulator 64, for example, through a second ferrule 65 placed and crimped around the tube 62 and the manipulator 64.

According to another example, the manipulation member 67 can be directly connected to the manipulator 64, omitting the ferrule 65. Thus, if the manipulator 64 has a cannular end, it can be put on the tube 62 and connected by a gluing, soldering and/or welding process.

To increase the binding surface, the manipulator 64 can be provided with one or more notches (not shown) through which a glue or soldering material can be delivered.

Figure 7:
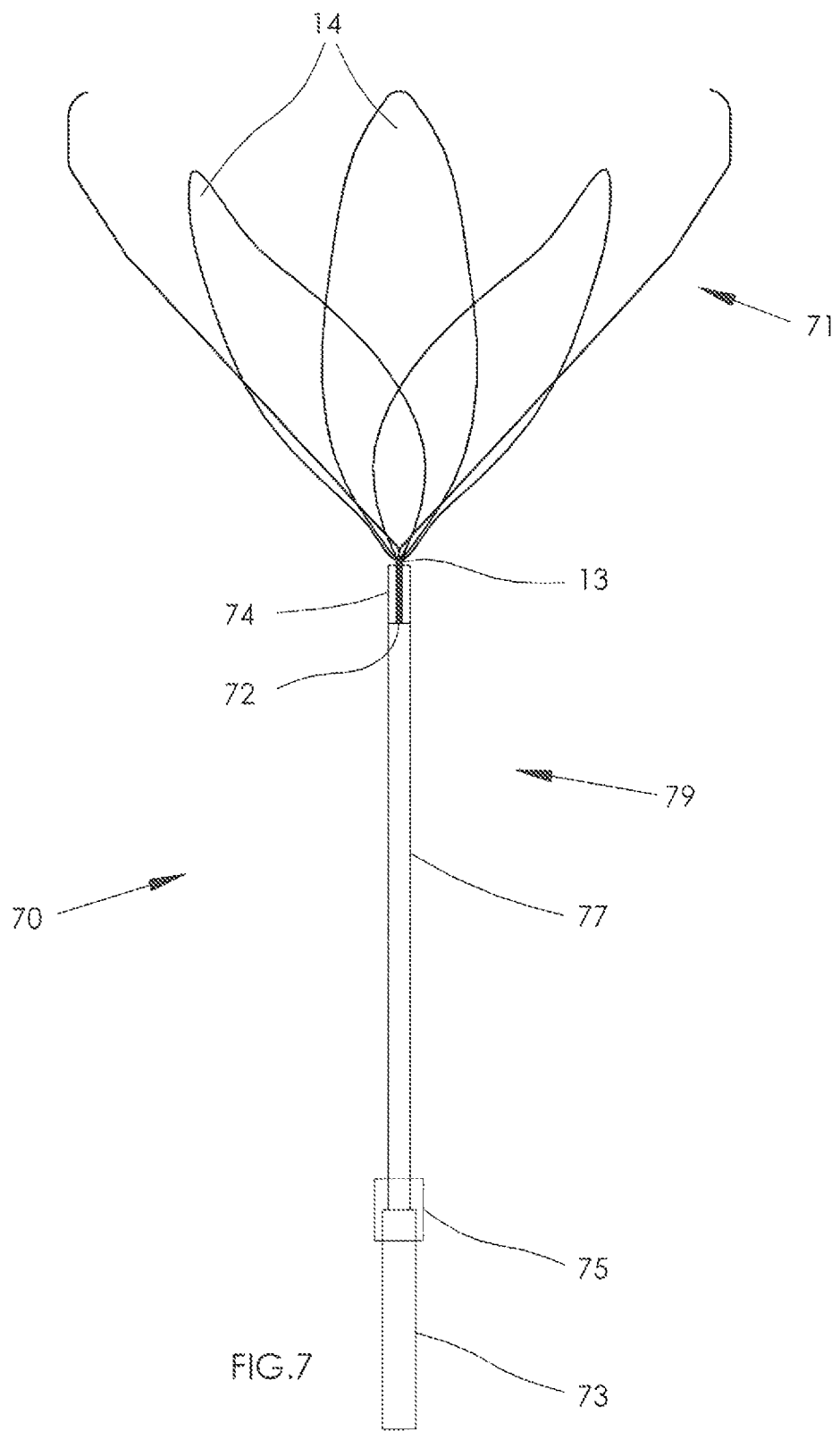
FIG. 7 illustrates a schematic view of connection of the loops of the retrieval snare shown in FIGS. 1A, 2A, 3, 4, 5A and 5B to a manipulation member, according to another embodiment of the invention.

Referring to FIG. 7, a schematic view of connection of a retrieval snare 71 to a pushing tube 77 in order to form a manipulation member 79 of the retrieval apparatus 70 is shown, according to another embodiment of the present invention. The retrieval snare 71 can be any retrieval snare described above. According to this embodiment, at least a part of the filaments which are extended from the end 13 are cut off at a predetermined distance from the end, thereby forming free filament ends 72. These free filament ends 72 are placed in a lumen of the pushing tube 77 and are crimped or welded together at a position 74, thereby to form a manipulation member. The pushing tube 77 of such a manipulation member can be connected to a manipulator 73, for example, by using a third ferrule 75 that is placed and crimped around the tube and the manipulator 73.

According to another example, the pushing tube 77 of the manipulation member can be directly connected to the manipulator 73 omitting the ferrule 75. Thus, the manipulator 73 can be put on the pushing tube 77 and connected by a gluing, soldering and/or welding process. As discussed above, the manipulator 73 can be provided with one or more notches (not shown) through which a glue or soldering material can be delivered to increase the binding surface area.

Figure 8:
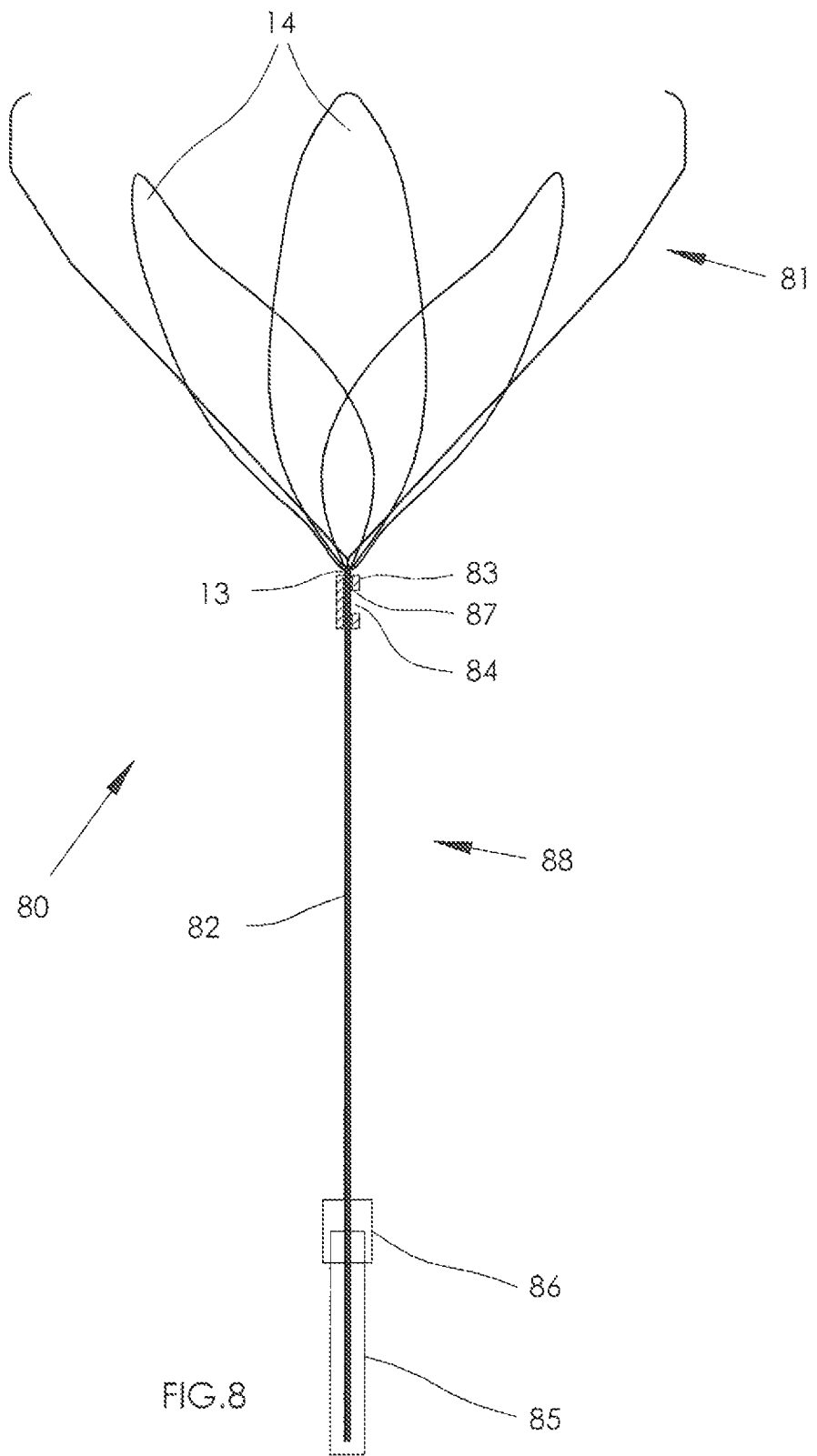
FIG. 8 illustrates a side view of a further embodiment of a manipulation member of the retrieval snare of the invention.

FIG. 8 shows yet another embodiment of a retrieval apparatus 80 including a manipulation member 88 associated with the retrieval snare 81 of the present invention. According to this embodiment, similar to the previous embodiment, the filaments that extend from the end 13 are cut off at a predetermined distance from the end to form free filament ends 87. The free filament ends 87 are connected to a pushing element 82. In this case, the pushing element 82 is formed in the form of a rod and operates analogously to the manipulation member (61 in FIG. 6).

For example, the connection of the pushing element 82 to the free filament ends 87 of the filaments can be implemented through welding or soldering. Likewise, the connection of the pushing element 82 to the free filament ends 87 of the filaments can be implemented through a fourth ferrule 83 placed and crimped around the pushing element 82 and around the free filament ends 87. When desired, the fourth ferrule 83 can include a notch 84 configured to facilitate connecting the pushing element 82 to the ferrule 83 by at least one connecting technique selected from soldering, welding and gluing.

The pushing element 82 can be connected to a manipulator 85, for example, by using a fifth ferrule 86 placed and crimped around the pushing element 82 and the manipulator 85. As described above, the pushing element 82 can also be directly connected to the manipulator 85, for example, by using a gluing, soldering or welding process.

The pushing element 82 of the manipulation member can, for example, be made of a metallic material, such as a NiTi based alloy or stainless steel. Likewise, the pushing element 82 can be made of a polymer material.

Figure 9:
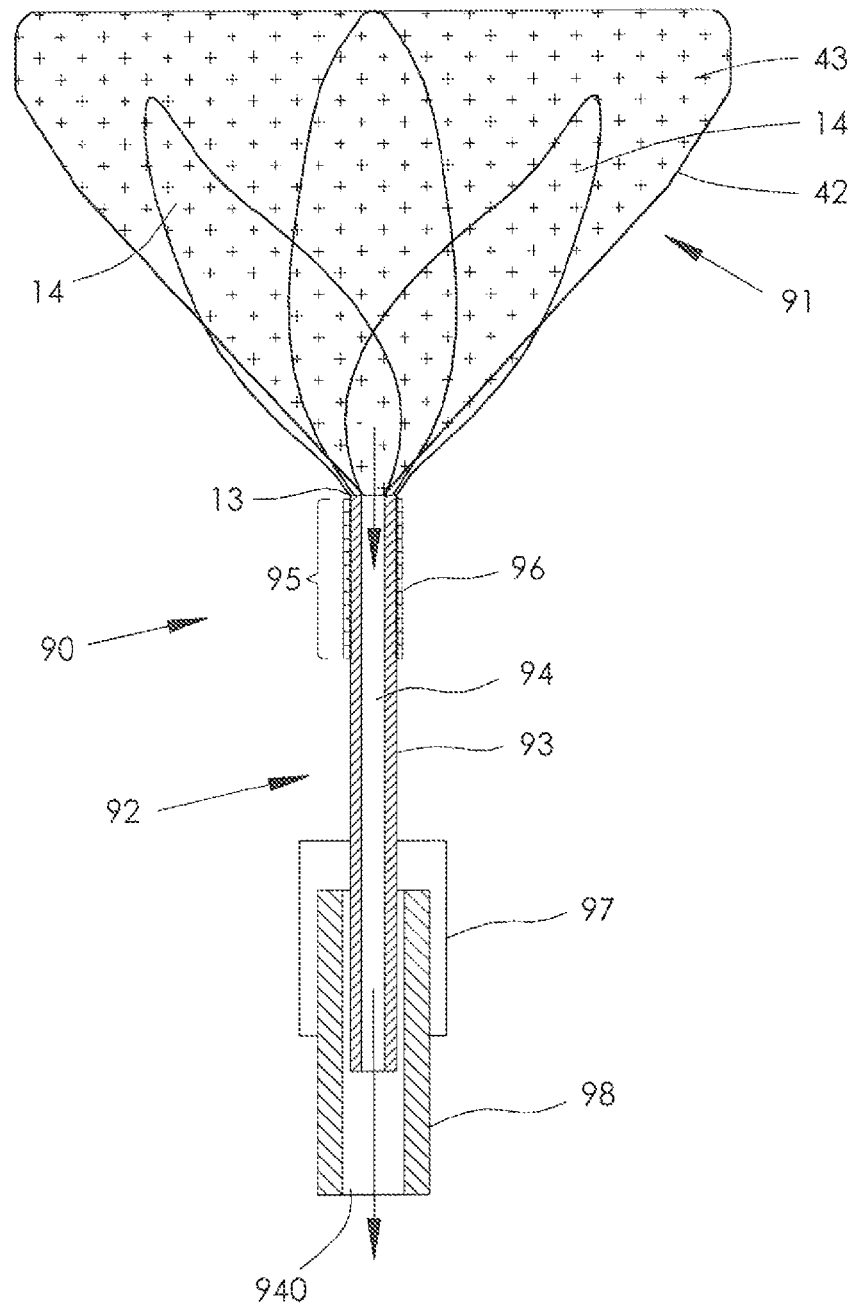
FIGS. 9, 10 and 11 illustrate a plan view of the distal part of a retrieval apparatus in a deployed position, according to still further embodiments of the present invention.

Referring to FIG. 9, a manipulation member 92 for a snare 91 of a retrieval apparatus 90 is shown, according to a further embodiment of the present invention. According to this embodiment, the manipulation member 92 includes an aspiration tube 93 coupled to the proximal end 13 of the snare 91. Coupling may be implemented either directly or through intermediate pushing members (not shown). The aspiration tube 93 includes an aspiration lumen 94 forming a channel through which various formations may be sucked out due to the creation of negative pressure (vacuum) by a suction device (not shown) coupled to the aspiration lumen 94.

The retrieval apparatus 90 can thereby be used as an aspiration device, when during the location of the device in a body, for example, in a blood vessel (not shown), small and relatively soft blood clots can be sucked out directly through the lumen 94 without entrapping them by the snare 91, whereas relatively large formations can first be captured and entrapped, and then be removed together with the snare 91 that is due to the special configuration described above can provide enhanced entrapping characteristics.

To increase the necessary negative pressure required for suction, the snare 91 can include a cover film 43 wrapping the carcass 42 formed of the filament loops 14, as described above in the embodiment shown in FIG. 4. It should be understood that the snare 91 with the carcass 42 wrapped with the cover film 43 can significantly enhance the aspiration properties of the apparatus, which is together with the improved entrapping characteristics can significantly augment effectiveness of retrieval apparatuses. The retrieval apparatus 90 can efficiently hold the captured object without its escape from the snare during operation.

The aspiration tube 93 can, for example, be made of polymeric material, such as polyimide, polyvinyl chloride, polytetrafluoroethylene, NYLON, TEFLON, etc. The aspiration tube 93 can also be made of a suitable metal (e.g., stainless steel, nitinol, etc.) or of composite materials. When desired, the aspiration tube 93 may be multi-layered with different materials, for example, a braided reinforced polyimide tube coated with polytetrafluoroethylene, thereby to provide a graduated bending and stiffness characteristic over its length.

At the snare proximal end 13, the filaments of the snare loops 14 can be trimmed and coupled to the aspiration tube 93 along the external surface circumference of the aspiration tube at its distal end by one or more connecting methods.

In one embodiment, the filaments of the snare loops 14 can be directly connected to the aspiration tube 93 at a joining portion 95 that can, for example, be in the range of 10 mm to 25 mm from the distal end of the aspiration tube 93. For instance, the filament may be soldered, brazed or welded to the aspiration tube 93 at the joining portion 95. Likewise, a medically-acceptable adhesive may also be used to secure or join the filament loops 14 to the aspiration tube 93. An example of the adhesive includes, but is not limited to, LOC-TITE® 4011 cyanoacrylate, epoxy glues, etc.

In order to increase mechanical strength of the joining portion 95, a thin tube 96 can be put on the filaments at the joining portion 95, as shown in FIG. 9. The tube 96 can, for example, be made of a thermo-shrinkable material. An example of the material suitable for the tube 96 includes but is not limited to polytetrafluoroethylene (PTFE), polyester, etc. The wall thickness of the tube 96 can, for example, be in the range of about 0.005 mm to 0.1 mm In another embodiment, a bounding ferrule (not shown) such as a hollow cannula, may be used to connect the filament loops 14 to the aspiration tube 93. The ferrule can be made of metal, e.g., stainless steel, etc. and be joined to the aspiration tube 93 and to the filaments, preferably, by soldering, welding or brazing, although other known techniques, such as gluing, may also be used. For instance, if soldering is used, the end of the aspiration tube 93 can first be etched, preferably with acid, followed by neutralizing and drying. Flux is then can be applied to both the aspiration tube 93 and the cannula, the two are soldered together, and excess solder is removed. Afterwards, the parts should be neutralized, dried and cleaned.

When desired, the snare control assembly can further include an additional pushing member 98 in the form of another tube axially connected to the aspiration tube 93 and having a common aspiration lumen 940 with the aspiration tube 93. An inner diameter of the additional pushing member 98 matches the outer diameter of the aspiration tube 93. The connection of the aspiration tube 93 to the additional pushing member 98 can, for example, be made by using a sixth ferrule 97. Alternatively, such connection can be made by using an adhesive or any other connecting technique.

Figure 10:
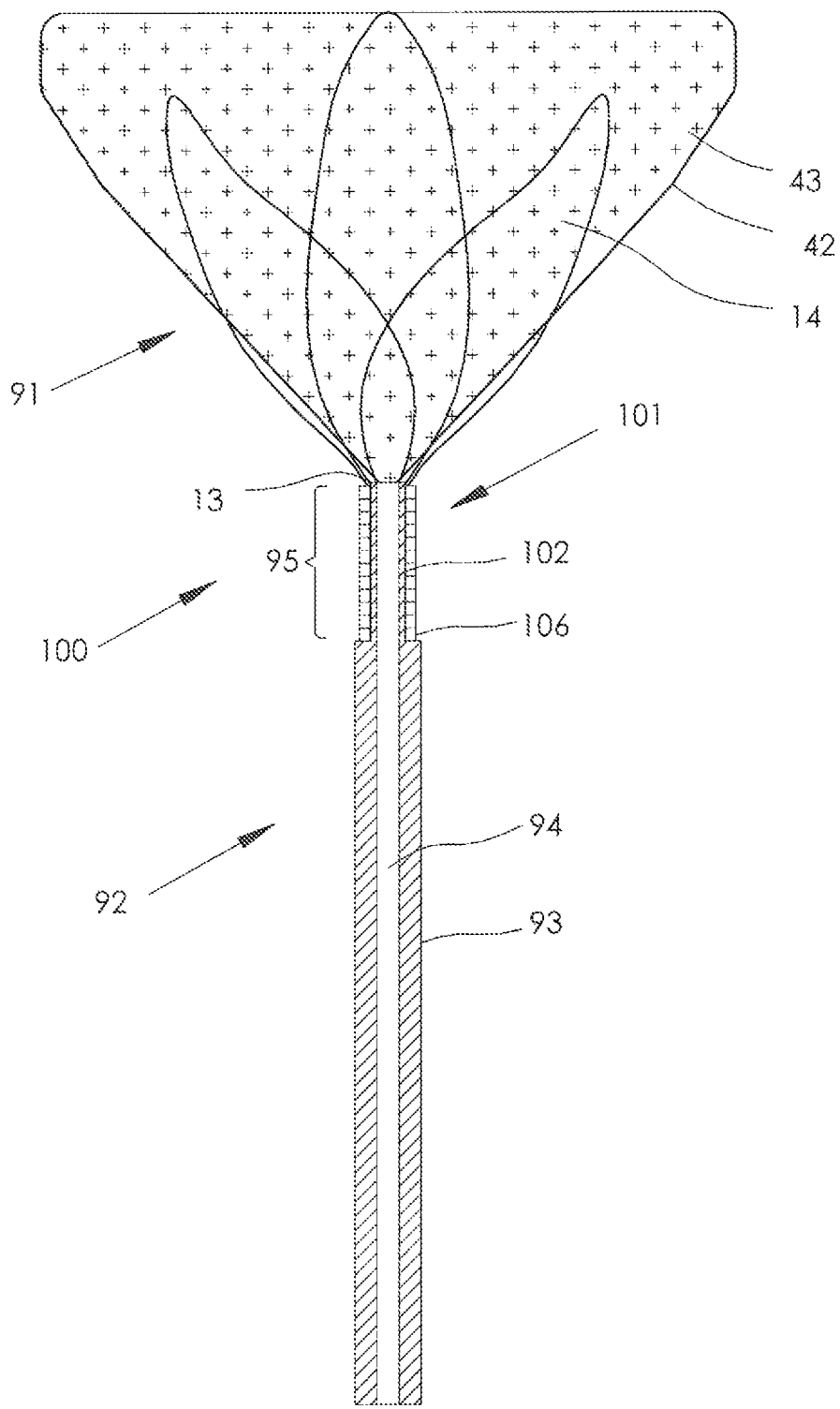

Referring to FIG. 10, a retrieval apparatus 100 is illustrated, according to still a further embodiment. This apparatus differs from the apparatus 90 in FIG. 9 in the fact that a hollow-out portion 101 is formed circumferentially on the external surface of a distal end of the aspiration tube 93 of the manipulation member 92 to define the joining portion 95. The filaments 102 of the snare loops 14 can be trimmed and directly connected (soldered, brazed or welded) to the hollow-out portion 101. A thin tube 106 can be put on the filaments at the joining portion 95, as shown in FIG. 10. This provision enables connecting of the snare to the aspiration tube 93 without increase of the aspiration tube diameter at the distal end.

Figure 11:
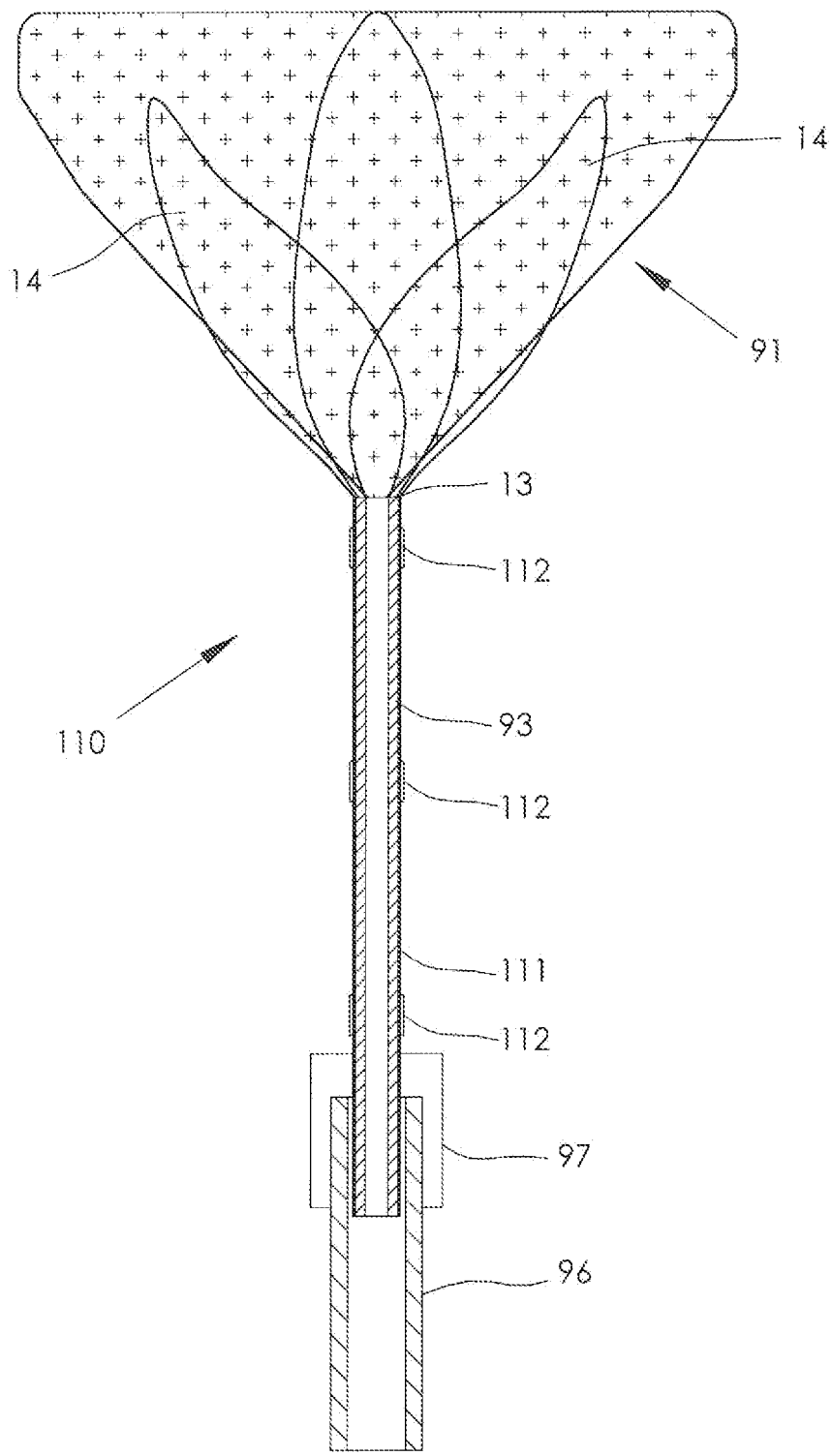

Referring to FIG. 11, a retrieval apparatus 110 is illustrated, which differs from the from the apparatus 90 in FIG. 9 and from apparatus 100 in FIG. 10 in the fact that at least a part of the filaments 111 extending from the proximal end 13 of the snare 91 are not cut-off, but rather extend axially along the external surface of the aspiration tube 93 and then extend further within the additional pushing member 98 to a proximal end of a manipulator (not shown). This feature is contemplated for security reasons, since in the case of breakage of the snare 91, it will be possible to pull the snare out from the patient's body (not shown), since the filaments come out at the proximal end (not shown) of the retrieval apparatus 110.

The filaments 111 can be connected to the external surface of the aspiration tube 93 and to the manipulator by any known technique. For example, bushing 112 may be used for connecting to the aspiration tube 93. Alternatively, a ferrule, a thermo-shrinkable tube or wrapping the filaments around the aspiration tube 93 and gluing them thereafter can be used to connect to filaments 111 to the manipulator.

In cardiovascular applications, a slim and flexible guide wire is sometimes employed which is introduced into the vascular system and manipulated by a physician through a body lumen until the guide wire enters the cavity of interest. Once the guide wire has been placed, the physician may then use the guide wire to pass other instruments into the patient. For instance, the proximal end of the guide wire may be placed in a lumen of a delivery catheter, which may then also be guided into the patient along the same guide wire that was previously placed.

Figure 12:
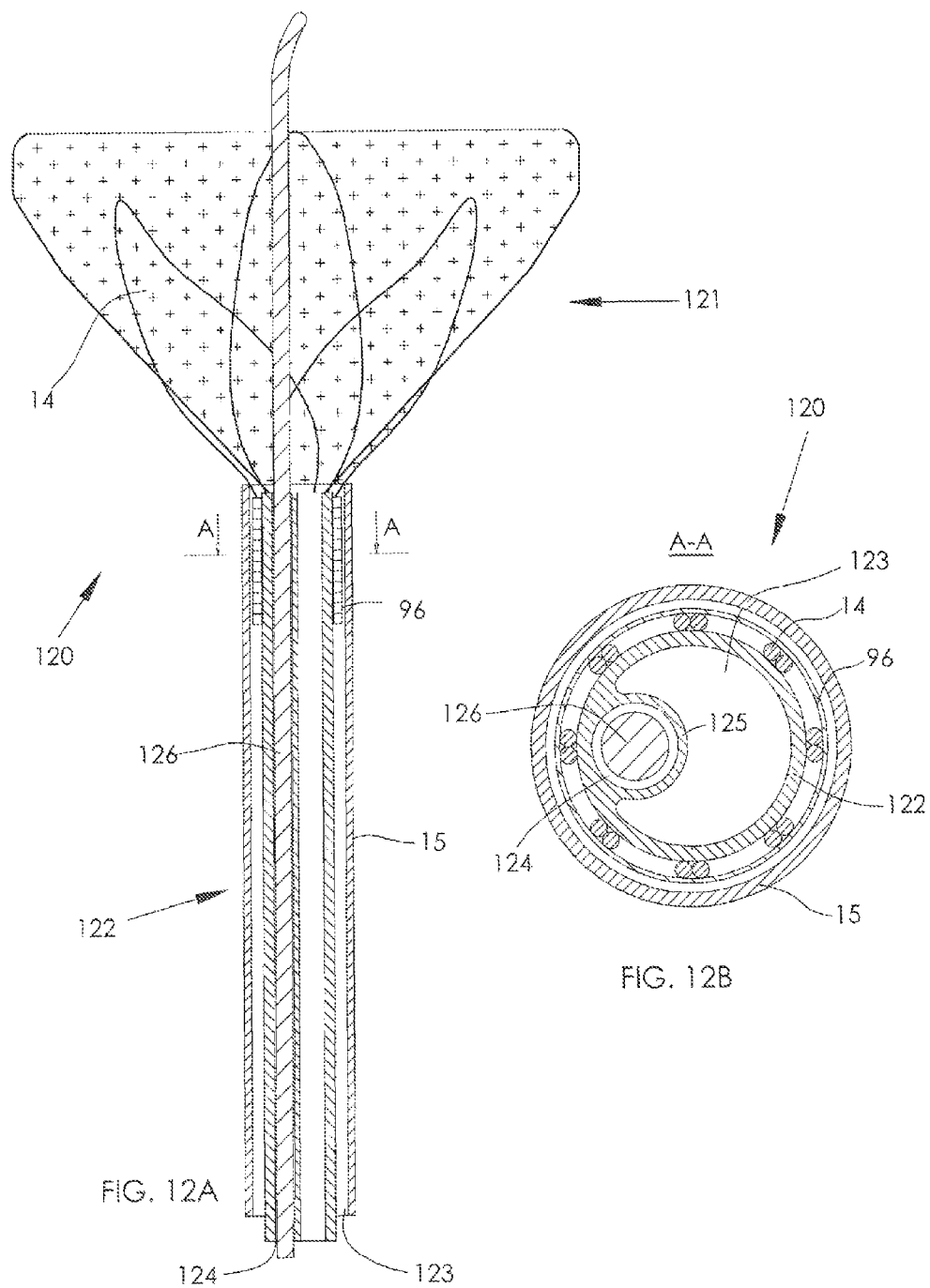
FIG. 12A illustrates a schematic longitudinal view of a distal portion of a retrieval apparatus, according to a further embodiment of the present invention.
FIG. 12B illustrates a schematic transverse cross-sectional fragmentary view of a distal portion of a retrieval apparatus of FIG. 12A taken along the line A-A.

Referring to FIGS. 12A and 12B together, a schematic longitudinal view and a transverse cross-sectional fragmentary view, respectively, of a distal portion of a retrieval apparatus 120 for entrapping and retaining an object (not shown) for its extraction from a body (not shown) are illustrated, according to yet a further embodiment of the present invention.

The retrieval apparatus 120 includes a retrieval snare 121 including a central structure with a plurality of filament loops 14 at a distal part of the apparatus 120 aggregated with a manipulation member 122 having two lumens, such as an aspiration lumen 123 and a wire guide lumen 124, which both extend between the proximal and distal ends of the manipulation member 122. As can be seen in FIG. 12B, the wire guide lumen 124 is arranged within the aspiration channel defined by the aspiration lumen 123 of the manipulation member 122 and separated from the aspiration lumen 123 by a separation wall 125.

The retrieval apparatus 120 also includes the delivery catheter 15, as described in the above embodiments. The wire guide lumen 124 is configured for accommodating a wire guide 126 during manipulation of the delivery catheter 15 into the patient's body (not shown).

Figure 13:
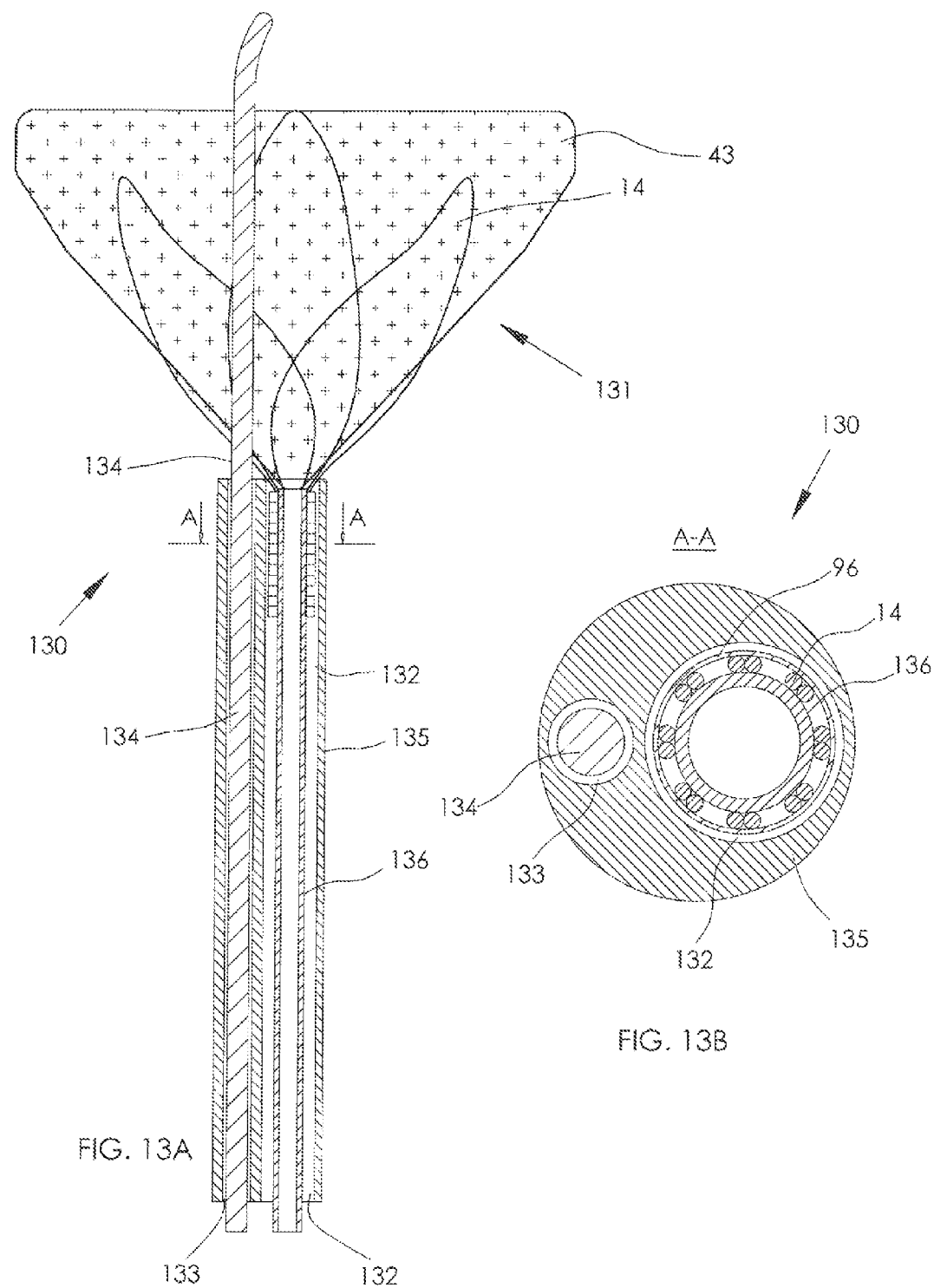
FIG. 13A illustrates a schematic longitudinal view of a distal portion of a retrieval apparatus, according to a further embodiment of the present invention.
FIG. 13B illustrates a schematic transverse cross-sectional fragmentary view of a distal portion of a retrieval apparatus of FIG. 13A taken along the line B-B.

Referring to FIGS. 13A and 13B together, a schematic longitudinal view and a transverse cross-sectional fragmentary view, respectively, of a distal portion of a retrieval apparatus 130 for entrapping and retaining an object for its extraction are illustrated, according to yet a further embodiment of the present invention.

The retrieval apparatus 130 includes a retrieval snare 131 including a central structure with a plurality of filament loops 14 at a distal part of the apparatus 130, and a delivery catheter 135 having a more complex structure than the delivery catheter 15 described in the above embodiments. The delivery catheter 135 differs from the delivery catheter 15 used in the above embodiments in the fact that the delivery catheter 135 includes two lumens, such as a snare lumen 132 and a wire guide lumen 133. Both lumens extend between the proximal and distal ends of the delivery catheter 135. The snare lumen 132 is configured to collapse the retrieval snare 131 when it is retracted inside of the delivery catheter 135 by pulling a manipulation member 136, as described above. The retrieval snare 131 and the manipulation member 136 can, for example, be the retrieval snare 91 shown in FIG. 9 or 10 which is used together with the manipulation member 92. In turn, the wire guide lumen 133 is configured for accommodating a wire guide 134 during manipulation of the delivery catheter 135 into the patient's body (not shown).

Figure 14:
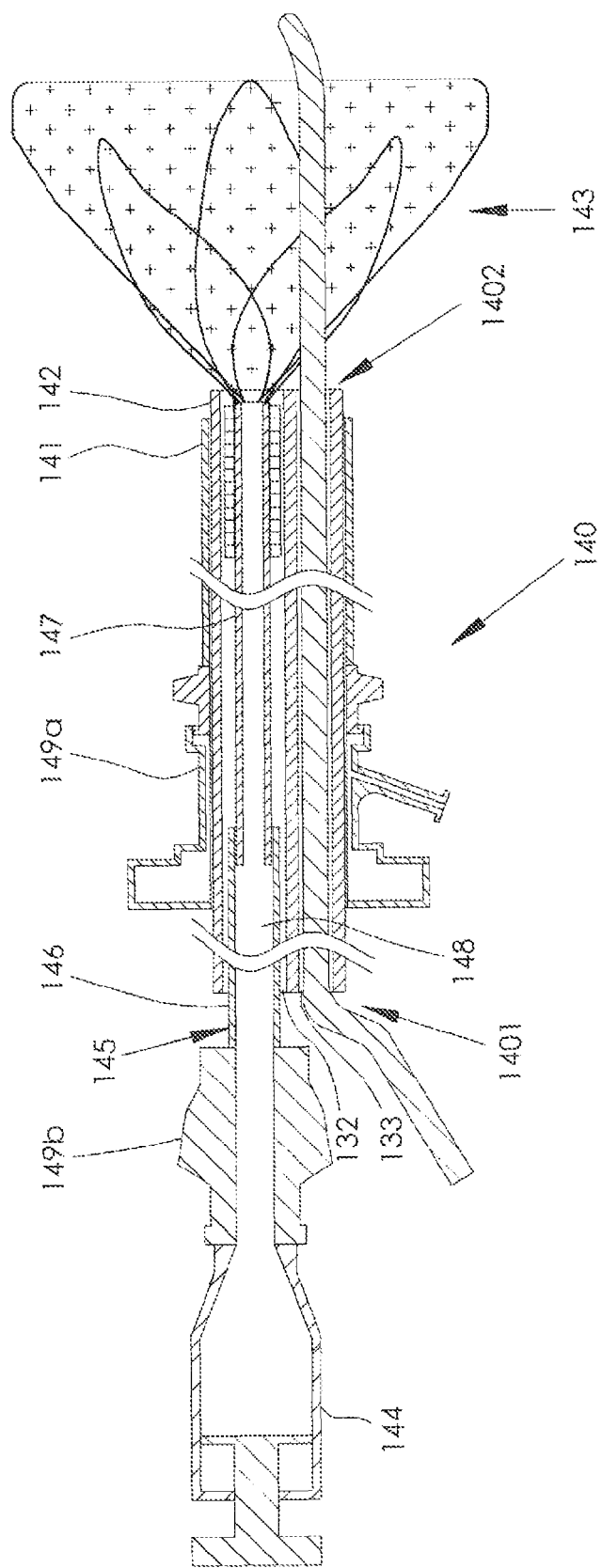
FIG. 14 illustrates a schematic longitudinal cross-sectional view of a fully assembled retrieval apparatus for entrapping and retaining an object for its extraction, according to a further embodiment of the present invention.

Referring to FIG. 14, a schematic longitudinal view of a retrieval apparatus 140 for entrapping and retaining an object (not shown) for its extraction is illustrated, according to still a further embodiment of the present invention. The retrieval apparatus 140 differs from the retrieval apparatus 120 in FIG. 12A and/or the retrieval apparatus 130 in FIG. 13A in the fact that it further includes a guiding catheter 141. The guiding catheter 141 includes a lumen for housing a delivery catheter 142. The lumen has sufficient size for receiving the distal end of the delivery catheter 142 therethrough together with a snare 143 in a contracted condition.

The guiding catheter 141 can be in the form of a thin-walled, cylindrical flexible tube adapted to penetrate into a body passage (not shown) to reach the desired location of an object. The guiding catheter 141 may be constructed from substantially flexible, durable, strong and/or floppy materials. For example, the guiding catheter 141 can be made of a flexible, durable, strong polymeric (e.g., plastic) material having a braid or other reinforcement (not shown) that sufficiently supports the guiding catheter 141 to prevent kinking or buckling, while allowing the guiding catheter 141 to be directed easily through tortuous vessel ducts. Examples of the polymer include, but are not limited to, polyimide, polyvinyl chloride, nylon, teflon, etc. The guiding catheter 141 can also be made of a composite material, such as a wire mesh or a coil, (e.g., stainless steel coil). When desired, the guiding catheter 141 may be multi-layered with different materials in order to provide a graduated bending and stiffness characteristic over its length.

As shown in FIG. 14, the retrieval apparatus 140 may further include a connector 149a configured for coupling the guiding catheter 141 to the delivery catheter 142. When desired, the connector 149a can also be configured for introducing a removal of contrast medium and prevent leakage of blood from the coronary sinus during coronary angiography.

The retrieval apparatus 140 also includes a suction device 144 on a proximal end of the retrieval apparatus 140. The suction device 144 can be coupled to a manipulation member 145 through a coupling bushing 149b. The manipulation member 145 includes an aspiration tube 147 axially connected to an additional pushing member 146 having a common aspiration lumen 148 with the aspiration tube 147. The suction device 144 is shaped as a handle to facilitate manipulation of the manipulation member 145, although other configurations are contemplated.

According to one embodiment, the manipulation member 145 is in the form of the manipulation member 122 having two lumens, such as the aspiration lumen 148 and the wire guide lumen 133, which both extend in parallel between the proximal and distal ends of the manipulation member 145, as described above with reference to FIGS. 12A and 12B. In this case, the delivery catheter 142 is the delivery catheter 15, as described in the above embodiments. A guide wire (126 in FIG. 12A) enters through an entrance port 1401 arranged at the proximal end of the manipulation member 145, extends through the entire wire guide lumen 133 and exits through an exit port 1402 arranged at the distal end of the manipulation member 145. It should be understood that when desired, the exit port can be arranged on a lateral side of the manipulation member 145.

According to another embodiment, the manipulation member 145 is the manipulation member 136 described above with reference to FIGS. 13A and 13B. In this case, the manipulation member 145 includes sole aspiration lumen 148 forming a channel through which various formations may be sucked out by the suction pump 144. But, in this case, the delivery catheter 142 is the delivery catheter (135 in FIGS. 13A and 13B) which includes two lumens, such as the snare lumen 132 and the wire guide lumen 133.

In this case, a guide wire (134 in FIG. 13A) enters through an entrance port 1401 arranged at the proximal end of the delivery catheter 142, extends through the entire wire guide lumen 133 and exits through a exit port 1402 arranged at the distal end of the delivery catheter 142. It should be understood that although the entrance port 1401 is shown in FIG. 14 at the proximal end of the delivery catheter 142, when desired, alternative entrance port (not shown) can be arranged on a lateral side of the delivery catheter 142.

From the foregoing description it should be appreciated that retrieval apparatus constructed in accordance with the present invention can comprise a variety of user desired shapes, number of loops, shape of the loops, types of connection of the loops in the proximal portion and types of connection of the loops to a manipulation member. Thus, although the exemplary snares 10 and 20 having eight filament loops 14 and 24 are illustrated in FIGS. 1A-1C and FIGS. 2A and 2B, respectively, showing the snares in accordance with different embodiments, the invention is not limited by such snare structures. Generally, any desired number of the loops equal to or greater than two may be employed, mutatis mutandis.

As such, those skilled in the art to which the present invention pertains, can appreciate that while the present invention has been described in terms of preferred embodiments, the concept upon which this disclosure is based may readily be utilized as a basis for the designing of other structures and processes for carrying out the several purposes of the present invention.

It should be understood that the snare of the present invention is not limited to medical treatment of a human body. It can be successfully employed for medical treatments of animals as well. Furthermore, the device of the invention is suitable for retrieval of objects from various cavities in body systems, for example, from blood vessels, the urinary tract, etc.

Moreover, the present invention is not limited to fabrication of medical devices, thus the retrieval apparatus of the invention can be used to extract any type of article from a wide range of inaccessible locations such as inside a pipe or tube (for example, the waste outlet of a domestic sink) or inside a chamber within a large piece of machinery which would be difficult to dismantle.

Also, it is to be understood that the phraseology and terminology employed herein are for the purpose of description and should not be regarded as limiting.

In the method claims that follow, alphabetic characters used to designate claim steps are provided for convenience only and do not imply any particular order of performing the steps.

It is important, therefore, that the scope of the invention is not construed as being limited by the illustrative embodiments set forth herein. Other variations are possible within the scope of the present invention as defined in the appended claims and their equivalents.

The invention claimed is:

1. A retrieval apparatus for entrapping and retaining an object located in a body for its extraction therefrom, the apparatus comprising a retrieval snare formed by a plurality of filaments defining proximal and distal sections interconnected to each other; the snare being changeable between its deployed state and contracted state; wherein the filaments extend from a proximal end of the proximal section towards the distal section, and then return to the proximal end to form a plurality of loops, the loops are interlaced with each other only within the proximal section, while being free within the distal section in the deployed state, distal ends of the loops approach each other when the snare is in the contracted state; wherein the filament loops are flat and planar along at least a portion of their length; and wherein sides of at least a part of the filament loops are bent within the distal section and arcuate into arcs at a distal end of the distal section such that said retrieval snare in the contracted state forms a hollow cavity at least at the distal section, wherein the filaments forming sides of the loops are bent three times to define four straight wire segments angled with respect to each other at a sequence of three angles having predetermined values.

2. The retrieval apparatus of claim 1, further comprising a snare control assembly comprising:
a delivery catheter having at least one lumen, and configured to penetrate into the body for reaching the object; and
a manipulation member coupled to the snare, and configured to path within said at least one lumen of the delivery catheter, and to operate for (i) protracting the snare from the delivery catheter for opening the snare and (ii) retracting the snare within the delivery catheter for collapsing the retrieval snare inside of the delivery catheter.

3. The retrieval apparatus of claim 2, wherein the snare further includes a mesh formed by interweaved and/or overlapping wires weaved around a snare carcass structure formed by said plurality of filaments.

4. The retrieval apparatus of claim 2, wherein the snare further includes a cover film configured for coating a snare carcass structure formed by the filaments.

5. The retrieval apparatus of claim 4, wherein the manipulation member includes an aspiration tube coupled to the filament loops at the proximal end of the snare along an external surface circumference of the aspiration tube.

6. The retrieval apparatus of claim 5, wherein the manipulation member includes an aspiration lumen and a guide wire lumen, both lumens extending between the proximal and distal ends of the manipulation member.

7. The retrieval apparatus of claim 6, wherein the wire guide lumen is arranged within the aspiration lumen and separated from the aspiration lumen by a separation wall.

8. The retrieval apparatus of claim 6, further comprising a guiding catheter including a lumen configured for housing the delivery catheter, a guide wire extending within the guide wire lumen; and a suction device coupled to the aspiration lumen at the proximal end of the manipulation member.

9. The retrieval apparatus of claim 5, wherein the delivery catheter includes a snare lumen and a guide wire lumen, both lumens extending between the proximal and distal ends of the delivery catheter.

10. The retrieval apparatus of claim 9, further comprising a guiding catheter including a lumen configured for housing the delivery catheter, a guide wire extending within the guide wire lumen; and a suction device coupled to the aspiration lumen at the proximal end of the delivery catheter.

11. The retrieval apparatus of claim 5 configured for withdrawing thromboembolic material.

12. The retrieval apparatus of claim 4, wherein the cover film has radiopaque properties.

13. The retrieval apparatus of claim 2, wherein the manipulation member includes at least a part of the plurality of filaments extending from the snare proximal end.

14. The retrieval apparatus of claim 2, wherein the manipulation member includes a pushing tube containing at least a part of the plurality of filaments axially disposed within a lumen of the pushing tube along at least a portion of the tube's length.

15. The retrieval apparatus of claim 1, wherein said predetermined values of said sequence of three angles counted from the snare proximal end are in the range of 160-175 degrees, 125-165 degrees, and 95-170 degrees, respectively.

16. The retrieval apparatus of claim 1, wherein an opening angle of the loops in a fully deployed state is in the range of about 60 degrees to about 130 degrees.

17. The retrieval apparatus of claim 16, wherein the angle ($\delta$) between the first and second straight wire segments ($L_1$ and $L_2$) deviates from the opening angle ($\theta$) of the loops in the fully deployed state by 30 to 115 degrees.

18. The retrieval apparatus of claim 1, wherein the angle ($\epsilon$) between the second and third straight wire segments ($L_2$ and $L_3$) deviates from the angle ($\delta$) between the first and second straight wire segments ($L_1$ and $L_2$) by 0 to 50 degrees.

19. The retrieval apparatus of claim 1, wherein a relationship between said predetermined values of said sequence of three angles is such that a direction of the third segment counted from the snare proximal end is coaxial with the direction of the delivery catheter.

20. The retrieval apparatus of claim 1, wherein a length of the first segment counted from the snare proximal end is greater than the length of the second segment by two to six times.

21. The retrieval apparatus of claim 1, wherein a length of the second segment counted from the snare proximal end is equal to or longer than the length of the third segment by up to two times.

22. The retrieval apparatus of claim 1, wherein at least one loop has a side that is permanently connected along the proximal portion to an opposite side of an adjacent loop at more than one connection point.

23. The retrieval apparatus of claim 22, wherein the permanent connection is carried out by twisting each pair of the filaments.

24. The retrieval apparatus of claim 1, wherein each side of each loop is permanently connected to a side of an adjacent loop near the proximal end along a predetermined segment length.

25. The retrieval apparatus of claim 1, wherein the loops are permanently interconnected to each other at least at one additional joint point selected within the proximal section in places where one loop crosses another loop.

26. The retrieval apparatus of claim 1, wherein a part of the filament loops is made of a thicker wire than the wire of the remaining loops.

27. The retrieval apparatus of claim 1, wherein at least a part of the filament loops have dimensions and shapes different from the dimensions and shapes of the other loops.

28. The retrieval apparatus of claim 1, wherein the snare further includes a closing element arranged at a distal section and configured for binding the loops together at their distal ends.

29. The retrieval apparatus of claim 1 wherein the filaments are made of metallic material.

30. The retrieval apparatus of claim 29, wherein the metallic material has thermo-mechanical shape memory and supereleastic characteristics.

31. The retrieval apparatus of claim 29, wherein the metallic material is one of NiTi based alloy and stainless steel.

32. The retrieval apparatus of claim 29, wherein the metallic material includes a radiopaque material.

33. The retrieval apparatus of claim 32, wherein the radiopaque material is at least one of the following metals: Pt, Au, Ag, Pd, Ta, W, Nb, Co, and Cu.

34. The retrieval apparatus of claim 1, wherein the filaments are made of non-metallic material.

35. The retrieval apparatus of claim 34, wherein the non-metallic material comprises one of Capron and Nylon.

36. The retrieval apparatus of claim 1 wherein said filaments are made of a core tube containing an axially disposed radiopaque wire.

37. The retrieval apparatus of claim 1, wherein the filaments are covered by a coating layer.

38. The retrieval apparatus of claim 37, wherein said coating layer is made of a radiopaque material.

39. The retrieval apparatus of claim 1, wherein parts of the filaments are covered by radiopaque coils.

40. The retrieval apparatus of claim 1, comprising at least one radiopaque, marker attached to at least one loop in said distal portion.

41. The retrieval apparatus of claim 40, wherein the radiopaque marker is a ferrule placed around the filament.

42. The retrieval apparatus of claim 1 wherein the filaments are multiwire strands.

43. The retrieval apparatus of claim 42 wherein said multiwire strands include a central core wire and at least one other wire twisted about said central core wire.

44. The retrieval apparatus of claim 43, wherein said other wire is made of a material having a level of radiopacity greater than the level of radiopacity of said central core wire.

45. A retrieval apparatus for entrapping and retaining an object located in a body for its extraction therefrom, the apparatus comprising a retrieval snare formed by a plurality of filaments defining proximal and distal sections interconnected to each other; the snare being changeable between its deployed state and contracted state; wherein the filaments extend from a proximal end of the proximal section towards the distal section, and then return to the proximal end to form a plurality of loops, the loops are interlaced with each other only within the proximal section, while being free within the distal section in the deployed state, distal ends of the loops approach each other when the snare is in the contracted state; wherein the filament loops are flat and planar along at least a portion of their length; and wherein sides of at least a part of the filament loops are bent within the distal section and arcuate into arcs at a distal end of the distal section such that said retrieval snare in the contracted state forms a hollow cavity at least at the distal section; wherein an interlaced pattern of the proximal section is formed by interleaving each lateral side of the filament loops with three corresponding opposite sides of the three neighboring loops arranged in a series.

* * * * *